US006218109B1

(12) United States Patent
Elledge et al.

(10) Patent No.: US 6,218,109 B1
(45) Date of Patent: Apr. 17, 2001

(54) MAMMALIAN CHECKPOINT GENES AND PROTEINS

(75) Inventors: Stephen J. Elledge; Yolanda Sanchez, both of Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 08/924,183

(22) Filed: Sep. 5, 1997

(51) Int. Cl.$^7$ ............................ C12Q 1/68; C12N 15/63; C12N 1/20; C07H 21/04

(52) U.S. Cl. ........................ 435/6; 435/320.1; 435/252.1; 435/91.2; 536/23.1; 536/24.3

(58) Field of Search ......................... 435/6, 320.1, 252.1, 435/91.2; 536/23.1, 24.3

(56) References Cited

PUBLICATIONS

Sanchez et al. Science vol. 277, pp. 1497–1501, 1997.*

* cited by examiner

*Primary Examiner*—Lisa B. Arthur
*Assistant Examiner*—Jehanne Souaya
(74) *Attorney, Agent, or Firm*—Gardere & Wynne, LLP; Daniel F. Perez; Edwin Flores

(57) ABSTRACT

The present invention relates to the isolation of gene sequences encoding mammalian cell cycle checkpoints, as well as the expression of the encoded proteins using recombinant DNA technology. The expressed proteins are used to generate specific antibodies and to inhibit the growth of cells. The human checkpoint gene sequences are used as a probe for a portion of the chromosome associated with tumors and other malignancies, as well as growth and/or development deficiencies.

17 Claims, 8 Drawing Sheets ggcc gga cag tcc gcc gag gtg ctc ggt gga gtc atg gca gtg ccc ttt gtg gaa gac tgg
M A V P F V E D W
gac ttg gtg caa acc ctg gga gaa ggt gcc tat gga gaa gtt caa ctt gct gtg aat aga
D L V Q T L G E G A Y G E V Q L A V N R
gta act gaa gaa gca gtc gca gtg aag att gta gat atg aag cgt gcc gta gac tgt cca
V T E E A V A V K I V D M K R A V D C P
gaa aat att aag aaa gag atc tgt atc aat aaa atg cta aat cat gaa aat gta gta aaa
E N I K K E I C I N K M L N H E N V V K
ttc tat ggt cac agg aga gaa ggc aat atc caa tat tta ttt ctg gag tac tgt agt gga
F Y G H R R E G N I Q Y L F L E Y C S G
gga gag ctt ttt gac aga ata gag cca gac ata ggc atg cct gaa cca gat gct cag aga
G E L F D R I E P D I G M P E P D A Q R
ttc ttc cat caa ctc atg gca ggg gtg gtt tat ctg cat ggt att gga ata act cac agg
F F H Q L M A G V V Y L H G I G I T H R
gat att aaa cca gaa aat ctt ctg ttg gat gaa agg gat aac ctc aaa atc tca gac ttt
D I K P E N L L L D E R D N L K I S D F
ggc ttg gca aca gta ttt cgg tat aat aat cgt gag cgt ttg ttg aac aag atg tgt ggt
G L A T V F R Y N N R E R L L N K M C G
act tta cca tat gtt gct cca gaa ctt ctg aag aga aga gaa ttt cat gca gga cca gtt
T L P Y V A P E L L K R R E F H A E P V
gat gtt tgg tcc tgt gga ata gta ctt act gca atg ctc gct gga gaa ttg cca tgg gac
D V W S C G I V L T A M L A G E L P W D
caa ccc agt gac agc tgt cag gag tat tct gac tgg aaa gaa aaa aaa aca tac ctc aac
Q P S D S C Q E Y S D W K E K K T Y L N
cct tgg aaa aaa atc gat tct gct cct cta gct ctg ctg cat aaa atc tta gtt gag aat
P W K K I D S A P L A L L H K I L V E N
cca tca gca aga att acc att cca gac atc aaa aaa gat aga tgg tac aac aaa ccc ctc
P S A R I T I P D I K K D R W Y N K P L
aag aaa ggg gca aaa agg ccc cga gtc act tca ggt ggt gtg tca gag tct ccc agt gga
K K G A K R P R V T S G G V S E S P S G
ttt tct aag cac att caa tcc aat ttg gac ttc tct cca gta aac agt gct tct agt gaa
F S K H I Q S N L D F S P V N S A S S E
gaa aat gtg aag tac tcc agt tct cag cca gaa ccc cgc aca ggt ctt tcc tta tgg gat
E N V K Y S S S Q P E P R T G L S L W D
acc agc ccc tca tac att gat aaa ttg gta caa ggg atc agc ttt tcc cag ccc aca tgt
T S P S Y I D K L V Q G I S F S Q P T C
cct gat cat atg ctt ttg aat agt cag tta ctt ggc acc cca gga tcc tca cag aac ccc
P D H M L L N S Q L L G T P G S S O N P
tgg cag cgg ttg gtc aaa aga atg aca cga ttc ttt acc aaa ttg gat gca gac aaa tct
W Q R L V K R M T R F F T K L D A D K S
tat caa tgc ctg aaa gag act tgt gag aag ttg ggc tat caa tgg aag aaa agt tgt atg
Y Q C L K E T C E K L G Y Q W K K S C M
aat cag gtt act ata tca aca act gat agg aga aac aat aaa ctc att ttc aaa gtg aat
N Q V T I S T T D R R N N K L I F K V N
ttg tta gaa atg gat gat aaa ata ttg gtt gac ttc cgg ctt tct aag ggt gat gga ttg
L L E M D D K I L V D F R L S K G D G L
gag ttc aag aga cac ttc ctg aag att aaa ggg aag ctg att gat att gtg agc agc cag
E F K R H F L K I K G K L I D I V S S Q
aag gtt tgg ctt cct gcc aca tga tcg gac cat cgg ctc tgg gga atc ctg gtg aat ata
K V W L P A T
gtg ctg cta tgt tga cat tat tct tcc tag aga aga tta tcc tgt cct gca aac tgc aaa
tag tag ttc ctg aag tgt tca ctt ccc tgt tta tcc aaa cat ctt cca att tat ttt gtt
tgt tcg gca tac aaa taa tac cta tat ctt aat tgt aag caa aac ttt ggg gaa agg atg
aat aga att cat ttg att att tct tca tgt gtg ttt agt atc tga att tga aac tca tct
ggt gga aac caa gtt tca ggg gac atg agt ttt cca gct ttt ata cac acg tat ctc att
ttt atc aaa aca ttt tgt tt

*FIG. 1* gctt gtc gct gtg ctt gga gtc atg gca gtg cct ttt gtg gaa gac tgg gat ttg gtg caa
M A V P F V E D W D L V Q
act ttg gga gaa ggt gcc tat gga gaa gtt caa ctt gct gtg aat aga ata act gaa caa
T L G E G A Y G E V Q L A V N R I T E Q
gct gtt gca gtg aaa att gta gac atg aag cgg gcc ata gac tgt cca caa aat att aag
A V A V K I V D M K R A I D C P Q N I K
aaa gag atc tgc atc aat aaa atg tta agc cac gag aat gta gtg aaa ttc tat ggc cac
K E I C I N K M L S H E N V V K F Y G H
aag agg gaa ggc cat atc cag tat ctg ttt ctg gag tac tgt agt gga gga gaa ctt ttt
R R E G H I Q Y L F L E Y C S G G E L F
gat aga att gag cca gac ata ggg atg cct gaa caa gat gct cag agg ttc ttc cac caa
D R I E P D I G M P E Q D A Q R F F H Q
ctc atg gca ggg gtg gtt tat ctt cat gga att gga ata act cac agg gat att aaa cca
L M A G V V Y L H G I G I T H R D I K P
gaa aac ctc ctc ttg gat gaa agg gat aac ctc aaa atc tct gac ttt ggc ttg gca acg
E N L L L D E R D N L K I S D F G L A T
gta ttt cgg cat aat aat cgt gaa cgc tta ctg aac aag atg tgt ggg act tta cct tat
V F R H N N R E R L L N K M C G T L P Y
gtt gct ccg gag ctt cta aag aga aaa gaa ttt cat gca gaa cca gtt gat gtt tgg tcc
V A P E L L K R K E F H A E P V D V W S
tgt gga ata gta ctt act gca atg ttg gct gga gaa ttg ccg tgg gac cag ccc agt gat
C G I V L T A M L A G E L P W D Q P S D
agc tgt cag gaa tat tct gat tgg aaa gaa aaa aaa acc tat ctc aat cct tgg aaa aaa
S C Q E Y S D W K E K K T Y L N P W K K
att gat tct gct cct ctg gct ttg ctt cat aaa att cta gtt gag act cca tca gca agg
I D S A P L A L L H K I L V E T P S A R
atc acc atc cca gac att aag aaa gat aga tgg tac aac aaa cca ctt aac aga gga gca
I T I P D I K K D R W Y N K P L N R G A
aag agg cca cgc gcc aca tca ggt ggt atg tca gag tct tct agt gga ttc tct aag cac
K R P R A T S G G M S E S S S G F S K H
att cat tcc aat ttg gac ttt tct cca gta aat aat ggt tcc agt gaa gaa acc gtg aag
I H S N L D F S P V N N G S S E E T V K
ttc tct agt tcc cag cca gag ccg aga aca ggg ctt tcc ttg tgg gac act ggt ccc tcg
F S S S Q P E P R T G L S L W D T G P S
aac gtg gac aaa ctg gtt cag ggc atc agt ttt tcc cag cct acg tgt cct gag cat atg
N V D K L V Q G I S F S Q P T C P E H M
ctt gta aac agt cag tta ctc ggt acc cct gga ttt tca cag aac ccc tgg cag cgc ttg
L V N S Q L Q G T P G F S Q N P W Q R L
gtc aaa agg atg aca cga ttc ttt act aaa ttg gat gcg gac aaa tct tac caa tgc ctg
V K R M T R F F T K L D A D K S Y Q C L
aaa gag acc ttc gag aag ttg ggc tat cag tgg aag aag agt tgt atg aat cag gtt act
K E T F E K L G Y Q W K K S C M N Q V T
gta tca aca act gat aga aga aac aat aag ttg att ttc aaa ata aat ttg gta gaa atg
V S T T D R R N N K L I F K I N L V E M
gat gag aag ata ctg gtt gac ttc cga ctt tct aag ggt gat gga tta gag ttc aag aga
D E K I L V D F R L S K G D G L E F K R
cac ttc ctg aag att aaa ggg aag ctc agc gat gtt gtg agc agc cag aag gtt tgg ttt
H F L K I K G K L S D V V S S Q K V W F
cct gtt aca tga gga agc tgt cag ctc tgc aca ttc ctg gtg aat aga gtg ctg cta tgt
P V T *
gac att ttt ctt cct aga gaa gat tat cta ttc tgc aaa ctg caa aca ata gtt gtt gaa
gag ttc tct tcc cat tac cca aac atc ttc cga ttt gta gtg ttt ggc ata caa ata cta
atg tat ttt aat tgt atg taa tgc ttt ggg gaa agg atg gat caa att cat tag gta ttt
gtc cag ctg tct tta aat tgt ctg gat ttg aaa cca agt tat ggg ata ctt gag ttt gcc
agc ttt tat acc cat gta gta gta tca ctt ttg aaa aat caa aag ctt gtt tca tcc caa
gca aaa tat ttt ctt ctc tgc cta ttt aat tgt aag gat gaa taa aca cag acc ata tac
agt tga ttg gtt cat gaa tga ggc cag cca caa aaa tgt gta tgt taa tgt atg tac tgt
att ttc agt ttg ggt ata tgt gct gca caa ggg ctt gac ca

FIG. 2

```
                         SEQUENCE LISTING


<160> NUMBER OF SEQ ID NOS: 15

<210> SEQ ID NO 1
<211> LENGTH: 476
<212> TYPE: PRT
<213> ORGANISM: Homo sapiens

<400> SEQUENCE: 1

Met Ala Val Pro Phe Val Glu Asp Trp Asp Leu Val Gln Thr Leu Gly
  1               5                  10                  15

Glu Gly Ala Tyr Gly Glu Val Gln Leu Ala Val Asn Arg Val Thr Glu
             20                  25                  30

Glu Ala Val Ala Val Lys Ile Val Asp Met Lys Arg Ala Val Asp Cys
         35                  40                  45

Pro Glu Asn Ile Lys Lys Glu Ile Cys Ile Asn Lys Met Leu Asn His
     50                  55                  60

Glu Asn Val Val Lys Phe Tyr Gly His Arg Arg Glu Gly Asn Ile Gln
 65                  70                  75                  80

Tyr Leu Phe Leu Glu Tyr Cys Ser Gly Gly Glu Leu Phe Asp Arg Ile
                 85                  90                  95

Glu Pro Asp Ile Gly Met Pro Glu Pro Asp Ala Gln Arg Phe Phe His
            100                 105                 110

Gln Leu Met Ala Gly Val Val Tyr Leu His Gly Ile Gly Ile Thr His
        115                 120                 125
```

-continued

```
Arg Asp Ile Lys Pro Glu Asn Leu Leu Leu Asp Glu Arg Asp Asn Leu
    130                 135                 140

Lys Ile Ser Asp Phe Gly Leu Ala Thr Val Phe Arg Tyr Asn Asn Arg
145                 150                 155                 160

Glu Arg Leu Leu Asn Lys Met Cys Gly Thr Leu Pro Tyr Val Ala Pro
            165                 170                 175

Glu Leu Leu Lys Arg Arg Glu Phe His Ala Glu Pro Val Asp Val Trp
            180                 185                 190

Ser Cys Gly Ile Val Leu Thr Ala Met Leu Ala Gly Glu Leu Pro Trp
        195                 200                 205

Asp Gln Pro Ser Asp Ser Cys Gln Glu Tyr Ser Asp Trp Lys Glu Lys
    210                 215                 220

Lys Thr Tyr Leu Asn Pro Trp Lys Lys Ile Asp Ser Ala Pro Leu Ala
225                 230                 235                 240

Leu Leu His Lys Ile Leu Val Glu Asn Pro Ser Ala Arg Ile Thr Ile
            245                 250                 255

Pro Asp Ile Lys Lys Asp Arg Trp Tyr Asn Lys Pro Leu Lys Lys Gly
            260                 265                 270

Ala Lys Arg Pro Arg Val Thr Ser Gly Gly Val Ser Glu Ser Pro Ser
        275                 280                 285

Gly Phe Ser Lys His Ile Gln Ser Asn Leu Asp Phe Ser Pro Val Asn
    290                 295                 300

Ser Ala Ser Ser Glu Glu Asn Val Lys Tyr Ser Ser Ser Gln Pro Glu
305                 310                 315                 320

Pro Arg Thr Gly Leu Ser Leu Trp Asp Thr Ser Pro Ser Tyr Ile Asp
            325                 330                 335

Lys Leu Val Gln Gly Ile Ser Phe Ser Gln Pro Thr Cys Pro Asp His
            340                 345                 350

Met Leu Leu Asn Ser Gln Leu Leu Gly Thr Pro Gly Ser Ser Gln Asn
        355                 360                 365

Pro Trp Gln Arg Leu Val Lys Arg Met Thr Arg Phe Phe Thr Lys Leu
    370                 375                 380

Asp Ala Asp Lys Ser Tyr Gln Cys Leu Lys Glu Thr Cys Glu Lys Leu
385                 390                 395                 400

Gly Tyr Gln Trp Lys Lys Ser Cys Met Asn Gln Val Thr Ile Ser Thr
            405                 410                 415

Thr Asp Arg Arg Asn Asn Lys Leu Ile Phe Lys Val Asn Leu Leu Glu
            420                 425                 430

Met Asp Asp Lys Ile Leu Val Asp Phe Arg Leu Ser Lys Gly Asp Gly
        435                 440                 445

Leu Glu Phe Lys Arg His Phe Leu Lys Ile Lys Gly Lys Leu Ile Asp
    450                 455                 460

Ile Val Ser Ser Gln Lys Val Trp Leu Pro Ala Thr
465                 470                 475


<210> SEQ ID NO 2
<211> LENGTH: 476
<212> TYPE: PRT
<213> ORGANISM: Mus musculus

<400> SEQUENCE: 2

Met Ala Val Pro Phe Val Glu Asp Trp Asp Leu Val Gln Thr Leu Gly
  1               5                  10                  15

Glu Gly Ala Tyr Gly Glu Val Gln Leu Ala Val Asn Arg Ile Thr Glu
```

-continued

```
            20                  25                  30

Gln Ala Val Ala Val Lys Ile Val Asp Met Lys Arg Ala Ile Asp Cys
        35                  40                  45

Pro Gln Asn Ile Lys Lys Glu Ile Cys Ile Asn Lys Met Leu Ser His
    50                  55                  60

Glu Asn Val Val Lys Phe Tyr Gly His Arg Arg Glu Gly His Ile Gln
65                  70                  75                  80

Tyr Leu Phe Leu Glu Tyr Cys Ser Gly Gly Glu Leu Phe Asp Arg Ile
                85                  90                  95

Glu Pro Asp Ile Gly Met Pro Glu Gln Asp Ala Gln Arg Phe Phe His
            100                 105                 110

Gln Leu Met Ala Gly Val Val Tyr Leu His Gly Ile Gly Ile Thr His
        115                 120                 125

Arg Asp Ile Lys Pro Glu Asn Leu Leu Leu Asp Glu Arg Asp Asn Leu
    130                 135                 140

Lys Ile Ser Asp Phe Gly Leu Ala Thr Val Phe Arg His Asn Asn Arg
145                 150                 155                 160

Glu Arg Leu Leu Asn Lys Met Cys Gly Thr Leu Pro Tyr Val Ala Pro
                165                 170                 175

Glu Leu Leu Lys Arg Lys Glu Phe His Ala Glu Pro Val Asp Val Trp
            180                 185                 190

Ser Cys Gly Ile Val Leu Thr Ala Met Leu Ala Gly Glu Leu Pro Trp
        195                 200                 205

Asp Gln Pro Ser Asp Ser Cys Gln Glu Tyr Ser Asp Trp Lys Glu Lys
    210                 215                 220

Lys Thr Tyr Leu Asn Pro Trp Lys Lys Ile Asp Ser Ala Pro Leu Ala
225                 230                 235                 240

Leu Leu His Lys Ile Leu Val Glu Thr Pro Ser Ala Arg Ile Thr Ile
                245                 250                 255

Pro Asp Ile Lys Lys Asp Arg Trp Tyr Asn Lys Pro Leu Asn Arg Gly
            260                 265                 270

Ala Lys Arg Pro Arg Ala Thr Ser Gly Gly Met Ser Glu Ser Ser Ser
        275                 280                 285

Gly Phe Ser Lys His Ile His Ser Asn Leu Asp Phe Ser Pro Val Asn
    290                 295                 300

Asn Gly Ser Ser Glu Glu Thr Val Lys Phe Ser Ser Ser Gln Pro Glu
305                 310                 315                 320

Pro Arg Thr Gly Leu Ser Leu Trp Asp Thr Gly Pro Ser Asn Val Asp
                325                 330                 335

Lys Leu Val Gln Gly Ile Ser Phe Ser Gln Pro Thr Cys Pro Glu His
            340                 345                 350

Met Leu Val Asn Ser Gln Leu Leu Gly Thr Pro Gly Phe Ser Gln Asn
        355                 360                 365

Pro Trp Gln Arg Leu Val Lys Arg Met Thr Arg Phe Phe Thr Lys Leu
    370                 375                 380

Asp Ala Asp Lys Ser Tyr Gln Cys Leu Lys Glu Thr Phe Glu Lys Leu
385                 390                 395                 400

Gly Tyr Gln Trp Lys Lys Ser Cys Met Asn Gln Val Thr Val Ser Thr
                405                 410                 415

Thr Asp Arg Arg Asn Asn Lys Leu Ile Phe Lys Ile Asn Leu Val Glu
            420                 425                 430

Met Asp Glu Lys Ile Leu Val Asp Phe Arg Leu Ser Lys Gly Asp Gly
        435                 440                 445
```

-continued

```
Leu Glu Phe Lys Arg His Phe Leu Lys Ile Lys Gly Lys Leu Ser Asp
    450                 455                 460

Val Val Ser Ser Gln Lys Val Trp Phe Pro Val Thr
465                 470                 475


<210> SEQ ID NO 3
<211> LENGTH: 1761
<212> TYPE: DNA
<213> ORGANISM: Homo sapiens

<400> SEQUENCE: 3

ggccggacag tccgccgagg tgctcggtgg agtcatggca gtgccctttg tggaagactg      60

ggacttggag caaaccctgg gagaaggtgc ctatggagaa gttcaacttg ctgtgaatag     120

agtaactgaa gaagcagtcg cagtgaagat tgtagatatg aagcgtgccg tagactgtcc     180

agaaaatatt aagaaagaga tctgtatcaa taaaatgcta aatcatgaaa atgtagtaaa     240

attctatggt cacaggagag aaggcaatat ccaatattta tttctggagt actgtagtgg     300

aggagagctt tttgacagaa tagagccaga cataggcatg cctgaaccag atgctcagag     360

attcttccat caactcatgg caggggtggt ttatctgcat ggtattggaa taactcacag     420

ggatattaaa ccagaaaatc ttctgttgga tgaaagggat aacctcaaaa tctcagactt     480

tggcttggca acagtatttc ggtataataa tcgtgagcgt ttgttgaaca agatgtgtgg     540

tactttacca tatgttgctc cagaacttct gaagagaaga gaatttcatg cagaaccagt     600

tgatgtttgg tcctgtggaa tagtacttac tgcaatgctc gctggagaat tgccatggga     660

ccaacccagt gacagctgtc aggagtattc tgactggaaa gaaaaaaaaa catacctcaa     720

cccttggaaa aaaatcgatt ctgctcctct agctctgctg cataaaatct tagttgagaa     780

tccatcagca agaattacca ttccagacat caaaaaagat agatggtaca acaaacccct     840

caagaaaggg gcaaaaaggc cccgagtcac ttcaggtggt gtgtcagagt ctcccagtgg     900

attttctaag cacattcaat ccaatttgga cttctctcca gtaaacagtg cttctagtga     960

agaaaatgtg aagtactcca gttctcagcc agaaccccgc acaggtcttt ccttatggga    1020

taccagcccc tcatacattg ataaattggt acaagggatc agcttttccc agcccacatg    1080

tcctgatcat atgcttttga atagtcagtt acttggcacc ccaggatcct cacagaaccc    1140

ctggcagcgg ttggtcaaaa gaatgacacg attctttacc aaattggatg cagacaaatc    1200

ttatcaatgc ctgaaagaga cttgtgagaa gttgggctat caatggaaga aaagttgtat    1260

gaatcaggtt actatatcaa caactgatag gagaaacaat aaactcattt tcaaagtgaa    1320

tttgttagaa atggatgata aaatattggt tgacttccgg ctttctaagg gtgatggatt    1380

ggagttcaag agacacttcc tgaagattaa agggaagctg attgatattg tgagcagcca    1440

gaaggtttgg cttcctgcca catcttccta gagaagatta tcctgtcctg caaactgcaa    1500

atagtagttc ctgaagtgtt cacttccctg tttatccaaa catcttccaa tttattttgt    1560

ttgttcggca tacaaataat acctatatct taattgtaag caaaactttg ggaaaggat     1620

gaatagaatt catttgatta tttcttcatg tgtgtttagt atctgaattt gaaactcatc    1680

tggtggaaac caagtttcag ggacatgag ttttccagct tttatacaca cgtatctcat     1740

ttttatcaaa acattttgtt t                                              1761


<210> SEQ ID NO 4
<211> LENGTH: 1962
<212> TYPE: DNA
```

-continued

<213> ORGANISM: Mus musculus

<400> SEQUENCE: 4
gcttgtcgct gtgcttggag tcatggcagt gccttttgtg gaagactggg atttggtgca 60
aactttggga gaaggtgcct atggagaagt tcaacttgct gtgaatagaa taactgaaca 120
agctgttgca gtgaaaattg tagacatgaa gcgggccata gactgtccac aaaatattaa 180
gaaagagatc tgcatcaata aaatgttaag ccacgagaat gtagtgaaat tctatggcca 240
caggagggaa ggccatatcc agtatctgtt tctggagtac tgtagtggag gagaactttt 300
tgatagaatt gagccagaca tagggatgcc tgaacaagat gctcagaggt tcttccacca 360
actcatggca ggggtggttt atcttcatgg aattggaata actcacaggg atattaaacc 420
agaaaacctc ctcttggatg aaagggataa cctcaaaatc tctgactttg gcttggcaac 480
ggtatttcgg cataataatc gtgaacgctt actgaacaag atgtgtggga ctttacctta 540
tgttgctccg gagcttctaa agagaaaaga atttcatgca gaaccagttg atgtttggtc 600
ctgtggaata gtacttactg caatgttggc tggagaattg ccgtgggacc agcccagtga 660
tagctgtcag gaatattctg attggaaaga aaaaaaaacc tatctcaatc cttggaaaaa 720
aattgattct gctcctctgg ctttgcttca taaaattcta gttgagactc catcagcaag 780
gatcaccatc ccagacatta agaaagatag atggtacaac aaaccactta acagaggagc 840
aaagaggcca cgcgccacat caggtggtat gtcagagtct tctagtggat tctctaagca 900
cattcattcc aatttggact tttctccagt aaataatggt tccagtgaag aaaccgtgaa 960
gttctctagt tcccagccag agccgagaac agggctttcc ttgtgggaca ctggtccctc 1020
gaacgtggac aaactggttc agggcatcag tttttcccag cctacgtgtc ctgagcatat 1080
gcttgtaaac agtcagttac tcggtacccc tggattttca cagaacccct ggcagcgctt 1140
ggtcaaaagg atgacacgat tctttactaa attggatgcg gacaaatctt accaatgcct 1200
gaaagagacc ttcgagaagt tgggctatca gtggaagaag agttgtatga atcaggttac 1260
tgtatcaaca actgatagaa gaaacaataa gttgattttc aaaataaatt tggtagaaat 1320
ggatgagaag atactggttg acttccgact ttctaagggt gatggattag agttcaagag 1380
acacttcctg aagattaaag ggaagctcag cgatgttgtg agcagccaga aggtttggtt 1440
tcctgttaca tgaggaagct gtcagctctg cacattcctg gtgaatagag tgctgctatg 1500
tgacattttt cttcctagag aagattatct attctgcaaa ctgcaaacaa tagttgttga 1560
agagttctct tcccattacc caaacatctt ccgatttgta gtgtttggca tacaaatact 1620
aatgtatttt aattgtatgt aatgctttgg ggaaaggatg gatcaaattc attaggtatt 1680
tgtccagctg tctttaaatt gtctggattt gaaaccaagt tatgggatac ttgagtttgc 1740
cagcttttat acccatgtag tagtatcact tttgaaaaat caaaagcttg tttcatccca 1800
agcaaaatat tttcttctct gcctatttaa ttgtaaggat gaataaacac agaccatata 1860
cagttgattg gttcatgaat gaggccagcc acaaaaatgt gtatgttaat gtatgtactg 1920
tattttcagt ttgggtatat gtgctgcaca agggcttgac ca 1962

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
<220> FEATURE:
<221> NAME/KEY: misc_feature -continued

```
<222> LOCATION: (3)(6)
<223> OTHER INFORMATION: The nucleic acid in this position can be either
      a “t” or “c”.
<220> FEATURE:
<221> NAME/KEY: misc_feature
<222> LOCATION: (6)
<223> OTHER INFORMATION: The nucleic acid in this position can be either
      a “t” or “c”.
<220> FEATURE:
<221> NAME/KEY: misc_feature
<222> LOCATION: (13)
<223> OTHER INFORMATION: The nucleic acid in this position can be either
      “t” or “c”.

<400> SEQUENCE: 5

ggyggygagt ttyatggatt t                                               21


<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence:  Synthetic

<400> SEQUENCE: 6

ttggacaggc caaagtc                                                    17


<210> SEQ ID NO 7
<211> LENGTH: 476
<212> TYPE: PRT
<213> ORGANISM: Homo sapiens

<400> SEQUENCE: 7

Met Ala Val Pro Phe Val Glu Asp Asn Asp Leu Val Gln Thr Leu Gly
  1               5                  10                  15

Glu Gly Ala Val Gly Glu Val Gln Leu Ala Val Asn Arg Val Thr Glu
             20                  25                  30

Glu Ala Val Ala Val Lys Ile Val Asp Met Arg Arg Ala Val Asp Cys
         35                  40                  45

Pro Glu Asn Ile Lys Lys Glu Ile Cys Ile Asn Lys Met Leu Asn Asn
     50                  55                  60

Glu Asn Val Val Lys Phe Tyr Gly His Arg Arg Arg Glu Gly Asn Ile
 65                  70                  75                  80

Gln Tyr Leu Phe Leu Glu Tyr Cys Ser Gly Gly Glu Leu Phe Asp Arg
                 85                  90                  95

Ile Glu Pro Asp Ile Gly Met Pro Glu Pro Asp Ala Gln Arg Phe Phe
            100                 105                 110

His Gln Leu Met Ala Gly Val Val Tyr Leu His Gly Ile Gly Ile Thr
        115                 120                 125

His Arg Asp Ile Lys Pro Glu Asn Leu Leu Leu Asp Glu His Asp Asn
    130                 135                 140

Leu Lys Ile Ser Asp Phe Gly Leu Ala Thr Val Phe Arg Tyr Asn Asn
145                 150                 155                 160

Arg Glu Arg Leu Leu Asn Lys Met Cys Gly Thr Leu Pro Tyr Val Ala
                165                 170                 175

Pro Glu Leu Leu Lys Arg Arg Glu Phe His Ala Glx Pro Val Asp Val
            180                 185                 190

Trp Ser Cys Gly Ile Val Leu Thr Ala Met Leu Ala Gly Glu Leu Pro
        195                 200                 205

Trp Asp Gln Pro Ser Asp Ser Cys Gln Glu Tyr Ser Asp Trp Lys Glu
    210                 215                 220
```

-continued

```
Lys Lys Thr Tyr Leu Asn Pro Trp Lys Lys Ile Asp Ser Ala Pro Leu
225                 230                 235                 240

Ala Leu Leu His Lys Ile Leu Val Glu Asn Pro Ser Ala Arg Ile Thr
                245                 250                 255

Ile Pro Asp Ile Lys Lys Asp Arg Trp Tyr Asn Lys Pro Leu Lys Lys
            260                 265                 270

Gly Ala Lys Arg Pro Arg Val Thr Ser Gly Gly Val Ser Glu Ser Pro
        275                 280                 285

Ser Gly Phe Ser Lys His Ile Gln Ser Asn Leu Asp Phe Ser Pro Val
    290                 295                 300

Asn Ser Ala Ser Ser Glu Glu Asn Val Lys Tyr Ser Ser Ser Gln Pro
305                 310                 315                 320

Glu Pro Arg Thr Gly Leu Ser Leu Trp Asp Thr Ser Pro Ser Tyr Ile
                325                 330                 335

Asp Lys Leu Val Gln Gly Ile Ser Phe Ser Gln Pro Thr Cys Pro Asp
            340                 345                 350

His Met Leu Leu Asn Ser Gln Leu Leu Gly Thr Pro Gly Ser Ser Gln
        355                 360                 365

Asn Pro Trp Gln Arg Leu Val Lys Arg Met Thr Arg Phe Phe Thr Lys
    370                 375                 380

Leu Asp Ala Asp Lys Ser Tyr Gln Cys Leu Lys Glu Thr Glu Lys Leu
385                 390                 395                 400

Gly Tyr Gln Trp Lys Lys Ser Cys Met Met Gln Val Thr Ile Ser Thr
                405                 410                 415

Thr Asp Arg Arg Asn Asn Lys Leu Ile Phe Lys Val Asn Leu Leu Glu
            420                 425                 430

Met Asp Asp Lys Ile Leu Val Asp Phe Arg Leu Ser Lys Gly Asp Gly
        435                 440                 445

Leu Glu Phe Lys Arg His Phe Leu Lys Ile Lys Gly Lys Leu Ile Asp
    450                 455                 460

Ile Val Ser Ser Gln Lys Val Trp Leu Pro Ala Thr
465                 470                 475


<210> SEQ ID NO 8
<211> LENGTH: 513
<212> TYPE: PRT
<213> ORGANISM: Drosophila melanogaster

<400> SEQUENCE: 8

Met Ala Ala Thr Leu Thr Glu Ala Gly Thr Gly Pro Ala Ala Thr Arg
  1               5                  10                  15

Glu Phe Val Glu Gly Trp Thr Leu Ala Gln Thr Leu Gly Glu Gly Ala
             20                  25                  30

Tyr Gly Glu Val Lys Leu Leu Ile Asn Arg Gln Thr Gly Gly Gly Cys
         35                  40                  45

Gly Met Lys Met Val Asp Leu Lys Lys His Pro Asp Ala Ala Asn Ser
     50                  55                  60

Val Arg Lys Glu Val Cys Ile Gln Lys Met Leu Gln Asp Lys His Ile
 65                  70                  75                  80

Leu Arg Phe Phe Gly Lys Arg Ser Gln Gly Ser Val Glu Tyr Ile Phe
                 85                  90                  95

Leu Glu Tyr Ala Ala Gly Gly Glu Leu Phe Asp Arg Ile Glu Pro Asp
            100                 105                 110

Val Gly Met Pro Gln His Glu Ala Gln Arg Tyr Phe Thr Gln Leu Leu
```

-continued

```
        115                 120                 125

Ser Gly Leu Asn Tyr Leu His Gln Arg Gly Ile Ala His Arg Asp Leu
    130                 135                 140

Lys Pro Glu Asn Leu Leu Leu Asp Glu His Asp Asn Val Lys Ile Ser
145                 150                 155                 160

Asp Phe Gly Met Ala Thr Met Phe Arg Cys Lys Gly Lys Glu Arg Leu
                165                 170                 175

Leu Asp Lys Arg Cys Gly Thr Leu Pro Tyr Val Ala Pro Glu Val Leu
            180                 185                 190

Gln Lys Ala Tyr Gln Pro Gln Pro Ala Asp Leu Trp Ser Cys Gly Val
        195                 200                 205

Ile Leu Val Thr Met Leu Ala Gly Glu Leu Pro Trp Asp Gln Pro Ser
    210                 215                 220

Thr Asn Cys Thr Glu Phe Thr Asn Trp Arg Asp Asn Asp His Trp Gln
225                 230                 235                 240

Leu Gln Thr Pro Trp Ser Lys Leu Asp Thr Leu Ala Ile Ser Leu Leu
                245                 250                 255

Arg Lys Leu Leu Leu Ala Thr Ser Pro Gly Thr Arg Leu Thr Leu Glu
            260                 265                 270

Lys Thr Leu Asp His Lys Trp Cys Asn Met Gln Phe Ala Asp Asn Glu
        275                 280                 285

Arg Ser Tyr Asp Leu Val Asp Ser Ala Ala Ala Leu Glu Ile Cys Ser
    290                 295                 300

Pro Lys Ala Lys Arg Gln Arg Leu Gln Ser Ser Ala His Leu Ser Asn
305                 310                 315                 320

Gly Leu Asp Asp Ser Ile Ser Arg Asn Tyr Cys Ser Gln Pro Met Pro
                325                 330                 335

Thr Met Arg Thr Asp Asp Asp Phe Asn Val Arg Leu Gly Ser Gly Arg
            340                 345                 350

Ile Gln Gly Gly Trp Arg Arg Pro Gln Thr Leu Ala Gln Glu Ala Arg
        355                 360                 365

Leu Ser Tyr Ser Phe Ser Gln Pro Ala Leu Leu Asp Asp Leu Leu Leu
    370                 375                 380

Ala Thr Gln Met Asn Gln Thr Gln Asn Ala Ser Gln Asn Tyr Phe Gln
385                 390                 395                 400

Arg Leu Val Arg Arg Met Thr Arg Phe Phe Val Thr Thr Arg Trp Asp
                405                 410                 415

Asp Thr Ile Lys Arg Leu Val Gly Thr Ile Glu Arg Leu Gly Gly Tyr
            420                 425                 430

Thr Cys Lys Phe Gly Asp Asp Gly Val Val Thr Val Ser Thr Val Asp
        435                 440                 445

Arg Asn Lys Leu Arg Leu Val Phe Lys Ala His Ile Ile Glu Met Asp
    450                 455                 460

Gly Lys Ile Leu Val Asp Cys Arg Leu Ser Lys Gly Cys Gly Leu Glu
465                 470                 475                 480

Phe Lys Arg Arg Phe Ile Lys Ile Lys Asn Ala Leu Glu Asp Ile Val
                485                 490                 495

Leu Lys Gly Pro Thr Thr Trp Pro Ile Ala Ile Ala Thr Asn Ser Val
            500                 505                 510

Pro
```

<210> SEQ ID NO 9
<211> LENGTH: 483

-continued

<212> TYPE: PRT
<213> ORGANISM: Caenorhabditis elegans

<400> SEQUENCE: 9

```
Met Ser Ala Ala Ser Thr Thr Ser Thr Pro Ala Ala Ala Ala Val Ala
  1               5                  10                  15
Pro Gln Gln Pro Glu Ser Leu Tyr Arg Val Val Gln Thr Leu Gly Glu
            20                  25                  30

Gly Ala Phe Gly Glu Val Leu Leu Ile Val Asn Thr Lys Asn Pro Glu
        35                  40                  45

Val Ala Ala Ala Met Lys Lys Ile Asn Ile Ala Asn Lys Ser Lys Asp
    50                  55                  60

Phe Ile Asp Asn Ile Arg Lys Glu Tyr Leu Leu Gln Lys Arg Val Ser
 65                  70                  75                  80

Ala Val Gly His Asp Asn Val Ile Arg Met Ile Gly Met Arg Asn Asp
                85                  90                  95

Pro Gln Phe Tyr Tyr Leu Phe Leu Glu Tyr Ala Asp Gly Gly Glu Leu
            100                 105                 110

Phe Asp Lys Ile Glu Pro Asp Cys Gly Met Ser Pro Val Phe Ala Gln
        115                 120                 125

Phe Tyr Phe Lys Gln Leu Ile Cys Gly Leu Lys Phe Ile His Asp Asn
    130                 135                 140

Asp Val Val His Arg Asp Ile Lys Pro Glu Asn Leu Leu Leu Thr Gly
145                 150                 155                 160

Thr His Val Leu Lys Ile Ser Asp Phe Gly Met Ala Thr Leu Tyr Arg
                165                 170                 175

Asn Lys Gly Glu Glu Arg Leu Leu Asp Leu Ser Cys Gly Thr Ile Pro
            180                 185                 190

Tyr Ala Ala Pro Glu Leu Cys Ala Gly Lys Lys Tyr Arg Gly Pro Pro
        195                 200                 205

Val Asp Val Trp Ser Ser Gly Ile Val Leu Ile Ala Met Leu Thr Gly
    210                 215                 220

Glu Leu Pro Trp Asp Arg Ala Ser Asp Ala Ser Gln Ser Tyr Met Gly
225                 230                 235                 240

Trp Ile Ser Asn Thr Ser Leu Asp Glu Arg Pro Trp Lys Lys Ile Asp
                245                 250                 255

Val Arg Ala Leu Cys Met Leu Arg Lys Ile Val Thr Asp Lys Thr Asp
            260                 265                 270

Lys Arg Ala Thr Ile Glu Gln Ile Gln Ala Asp Pro Trp Tyr Gln His
        275                 280                 285

Asn Phe Gly Gln Val Glu Thr Pro Asn Gly Arg Pro Leu Lys Arg Ala
    290                 295                 300

Arg Asn Asn Asp Glu Asn Ile Thr Cys Thr Gln Gln Ala Glu Cys Ser
305                 310                 315                 320

Ala Lys Arg Arg His Leu Glu Thr Pro Asn Glu Lys Ser Thr Leu Ala
                325                 330                 335

Glu Arg Gln Asn Ala Ser Phe Ser Gln Pro Thr Lys Thr Glu Asp Leu
            340                 345                 350

Leu Leu Thr Gln His Ile Asp Met Ser Gln Thr Asn Ser Asn Leu Leu
        355                 360                 365

Gln Arg Met Val Cys Arg Met Thr Arg Phe Cys Val Val Thr Asp Ile
    370                 375                 380

Arg Ser Thr Tyr Gln Lys Val Ala Arg Ala Ser Glu His Ala Gly Phe
385                 390                 395                 400
```

-continued

```
Gly Leu Arg Glu Thr Asp Asp Tyr Arg Leu Leu Val Thr Trp Arg Glu
                405                 410                 415

Val Ser Met Met Val Ser Leu Tyr Thr Met Gly Asp Ile Pro Asp Lys
            420                 425                 430

Pro Arg Val Met Val Asp Phe Arg Ser Leu Ala Val Thr Glu Ser Ser
        435                 440                 445

Leu Arg Arg Cys Ser Trp Thr Leu Glu Thr Val Cys Met Ser Gly Tyr
    450                 455                 460

Val Pro Thr Glu Thr Thr Gly Ser Pro Ile Leu Asp Met Cys Gln Glu
465                 470                 475                 480

Ile Arg Arg


<210> SEQ ID NO 10
<211> LENGTH: 496
<212> TYPE: PRT
<213> ORGANISM: Schizosaccharomyces pombe

<400> SEQUENCE: 10

Met Ala Gln Lys Leu Asp Asn Phe Pro Tyr His Ile Gly Arg Glu Ile
  1               5                  10                  15

Gly Thr Gly Ala Phe Ala Ser Val Arg Leu Cys Tyr Asp Asp Asn Ala
             20                  25                  30

Lys Ile Tyr Ala Val Lys Phe Val Asn Lys Lys His Ala Thr Ser Cys
         35                  40                  45

Met Asn Ala Gly Val Trp Ala Arg Arg Met Ala Ser Glu Ile Gln Leu
     50                  55                  60

His Lys Leu Cys Asn Gly His Lys Asn Ile Ile His Phe Tyr Asn Thr
 65                  70                  75                  80

Ala Glu Asn Pro Gln Trp Arg Trp Val Val Leu Glu Phe Ala Gln Gly
                 85                  90                  95

Gly Asp Leu Phe Asp Lys Ile Glu Pro Asp Val Gly Ile Asp Glu Asp
            100                 105                 110

Val Ala Gln Phe Tyr Phe Ala Gln Leu Met Glu Gly Ile Ser Phe Met
        115                 120                 125

His Ser Lys Gly Val Ala His Arg Asp Leu Lys Pro Glu Asn Ile Leu
    130                 135                 140

Leu Asp Tyr Asn Gly Asn Leu Lys Ile Ser Asp Phe Gly Phe Ala Ser
145                 150                 155                 160

Leu Phe Ser Tyr Lys Gly Lys Ser Arg Leu Leu Asn Ser Pro Val Gly
                165                 170                 175

Ser Pro Pro Tyr Ala Ala Pro Glu Ile Thr Gln Gln Tyr Asp Gly Ser
            180                 185                 190

Lys Val Asp Val Trp Ser Cys Gly Ile Ile Leu Phe Ala Leu Leu Leu
        195                 200                 205

Gly Asn Thr Pro Trp Asp Glu Ala Ile Ser Asn Thr Gly Asp Tyr Leu
    210                 215                 220

Leu Tyr Lys Lys Gln Cys Glu Arg Pro Ser Tyr His Pro Trp Asn Leu
225                 230                 235                 240

Leu Ser Pro Gly Ala Tyr Ser Ile Ile Thr Gly Met Leu Arg Ser Asp
                245                 250                 255

Pro Phe Lys Arg Tyr Ser Val Lys His Val Val Gln His Pro Trp Leu
            260                 265                 270

Thr Ser Ser Thr Pro Phe Arg Thr Lys Asn Gly Asn Cys Ala Asp Pro
        275                 280                 285
```

-continued

```
Val Ala Leu Ala Ser Arg Leu Met Leu Lys Leu Arg Ile Asp Leu Asp
    290                 295                 300

Lys Pro Arg Leu Ala Ser Ser Arg Ala Ser Gln Asn Asp Ser Gly Phe
305                 310                 315                 320

Ser Met Thr Gln Pro Ala Phe Lys Lys Asn Asp Gln Lys Glu Leu Asp
                325                 330                 335

Arg Val Glu Val Tyr Gly Ala Leu Ser Gln Pro Val Gln Leu Asn Lys
            340                 345                 350

Asn Ile Asp Val Thr Glu Ile Leu Glu Lys Asp Pro Ser Leu Ser Gln
        355                 360                 365

Phe Cys Glu Asn Glu Gly Phe Ile Lys Arg Leu Ala Lys Lys Ala Lys
    370                 375                 380

Asn Phe Tyr Glu Ile Cys Pro Pro Glu Arg Leu Thr Arg Phe Tyr Ser
385                 390                 395                 400

Arg Ala Ser Arg Glu Thr Ile Ile Asp His Leu Tyr Asp Ser Leu Arg
                405                 410                 415

Leu Leu Ala Ile Ser Val Thr Met Lys Tyr Val Arg Asn Gln Thr Ile
            420                 425                 430

Leu Tyr Val Asn Leu His Asp Lys Arg Lys Cys Leu Leu Gln Gly Val
        435                 440                 445

Ile Glu Leu Thr Asn Leu Gly His Asn Leu Glu Leu Ile Asn Phe Ile
    450                 455                 460

Lys Arg Asn Gly Asp Pro Leu Glu Trp Arg Lys Phe Phe Lys Asn Val
465                 470                 475                 480

Val Ser Ser Ile Gly Lys Pro Ile Val Leu Thr Asp Val Ser Gln Asn
                485                 490                 495


<210> SEQ ID NO 11
<211> LENGTH: 186
<212> TYPE: DNA
<213> ORGANISM: Artificial Sequence
<220> FEATURE:
<223> OTHER INFORMATION: Description of Artificial Sequence:  Synthetic

<400> SEQUENCE: 11

ggggggagc tgtttgaccg aatagagcca gacataggca tgcctgaacc agatgctcag     60

agattcttcc atcaactcat gggaggggtg gtttatctgc atggtattgg aataactcac    120

agggatatta aaccagaaaa tcttctgttg gaagaaaggg ataacctcaa aatctcagac    180

tttggc                                                               186


<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:  Synthetic

<400> SEQUENCE: 12

ctagaggagc agaatcg                                                    17


<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence:  Synthetic

<400> SEQUENCE: 13
```

-continued

```
gcagtttgca ggacaggata atcttctcta ggaag                           35


<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence:  Synthetic

<400> SEQUENCE: 14

ttgctccaga acttctg                                               17


<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence:  Synthetic

<400> SEQUENCE: 15

tattggttga cttccggc                                              18
```

MAMMALIAN CHECKPOINT GENES AND PROTEINS

FIELD OF THE INVENTION

The present invention relates to mammalian proteins and gene sequences involved in cellular responses to DNA damage. In particular, the present invention provides checkpoint genes and proteins.

BACKGROUND OF THE INVENTION

The proper development of a multicellular organism is a complex process that requires precise spatial and temporal control of cell proliferation. Cell proliferation in the embryo is controlled via an intricate network of extracellular and intracellular signaling pathways that process growth regulatory signals. This signaling network is superimposed upon the basic cell cycle regulatory machinery that controls particular cell cycle transitions.

Cell cycle checkpoints are regulatory pathways that control the order and timing of cell cycle transitions, and ensure that critical events such as DNA replication and chromosome segregation are completed with high fidelity. For example, proliferating eukaryotic cells arrest their progression through the cell cycle in response to DNA damage. This arrest is critical to the survival of the organism, as failure to repair damaged DNA can result in the formation and transfer of mutations, damaged chromosomes, cancer, or other detrimental effects. The mechanism responsible for monitoring the integrity of the organism's DNA and preventing the progression through the cell cycle when DNA damage is detected is referred to as the "DNA damage checkpoint."

In response to DNA damage, cells activate a checkpoint pathway that arrests the cell cycle, in order to provide time for repair, and induces the transcription of genes that facilitate the needed repair. In yeast, this checkpoint pathway consists of several protein kinases including phosphoinositide (PI)-kinase homologs hATM (human), scMec1 (*Saccharomyces cerevisiae*), spRad3 (*Schizosaccharomyces pombe*), and protein kinases scDun1 (*Saccharomyces cerevisiae*), scRad53 (*Saccharomyces cerevisiae*), and spChk1 (*Schizosaccharomyces pombe*) (See e.g., S. Elledge, Science 1664 [1996]).

Indeed, the ability to coordinate cell cycle transitions in response to genotoxic and other stressors is critical to the maintenance of genetic stability and prevention of uncontrolled cellular growth. Loss of a checkpoint gene leads to genetic instability and the inability of the cells to deal with genomic insults such as those suffered as a result of the daily exposure to ultraviolet radiation. The loss of negative growth control and improper monitoring of the fidelity of DNA replication are common features of tumor cells. When checkpoints are eliminated (e.g., by mutation or other means), cell death, infidelity in chromosome transmission, and/or increased susceptibility to deleterious environmental factors (e.g., DNA-damaging agents) result. A variety of abnormal cells arising due to infidelity during mitoses have been detected in humans, including aneuploidy, gene amplification, and multipolar mitoses (See, L. H. Hartwell and T. A. Weinert, Science 246:629 [1989]).

Accordingly, elucidation of checkpoint function, as well as the disruption of checkpoint function, will further the understanding of the process of cellular transformation (i.e., the conversion of normal cells to a state of unregulated growth), as well as cell differentiation and organismal development.

SUMMARY OF THE INVENTION

The present invention provides mammalian proteins and gene sequences involved in cellular responses to DNA damage. In particular, the present invention provides Chk1 genes and proteins.

In one embodiment, the present invention provides the nucleotide sequence set forth in SEQ ID NO:3. In alternative embodiments, the present invention provides SEQ ID NO:3, wherein it further comprises 5' and 3' flanking regions. In yet another embodiment, the sequence further comprises intervening regions. In a further embodiment, the present invention also provides a polynucleotide sequence which is complementary to SEQ ID NO:3 or variants thereof. In a preferred embodiment, the present invention provides a vector comprising the nucleotide sequence of claim 1. The present invention also provides host cell(s) containing the vector of claim 4.

The present invention also provides a purified Chk1 protein encoded by the nucleotide sequence of claim 1, as well as a purified protein comprising the amino acid sequence set forth in SEQ ID NO:1. In addition, the present invention provides fusion proteins comprising a least a portion of the human Chk1 protein, as well as non-Chk1 protein sequences. It is not intended that the fusion proteins of the present invention be limited to any particular portion of the Chk1 portion or any particular non-Chk1 protein sequences. In preferred embodiments, the fusion the Chk1 protein portion of the fusion protein comprises at least a portion of SEQ ID NO:1. In an alternative embodiment, the non-Chk1 protein sequence comprises an affinity tag. In particularly preferred embodiment, the affinity tag comprises a histidine tract.

In yet another embodiment, the present invention provides the sequence set forth in SEQ ID NO:4. In an alternative embodiment, the nucleotide sequence further comprises 5' and 3' flanking regions. In another alternative embodiment, the nucleotide sequence further comprises intervening regions. In yet another embodiment, the present invention provides a polynucleotide sequence that is complementary to SEQ ID NO:4 or variants thereof.

The present invention also provides a vector comprising the nucleotide sequence set forth in SEQ ID NO:4. In one preferred embodiment, the present invention provides a host cell containing the vector comprising this nucleotide sequence.

The present invention further provides a purified Chk1 protein encoded by the nucleotide sequence of SEQ ID NO:4. In yet another embodiment, the present invention provides a purified protein comprising the amino acid sequence set forth in SEQ ID NO:2.

The present invention also provides fusions proteins comprising at least a portion of the murine Chk1 protein and a non-Chk1 protein sequence. It is not intended that the fusion proteins of the present invention be limited to any particular portion of the Chk1 portion or any particular non-Chk1 protein sequences. In preferred embodiments, the fusion the Chk1 protein portion of the fusion protein comprises at least a portion of SEQ ID NO:2. In an alternative embodiment, the non-Chk1 protein sequence comprises an affinity tag. In particularly preferred embodiment, the affinity tag comprises a histidine tract.

The present invention also provides methods for detecting Chk1 protein. In one embodiment, the method comprises the steps of providing in any order: a sample suspected of containing the Chk1 protein; an antibody capable of specifically binding to a Chk1 protein; mixing the sample and the antibody under conditions wherein the antibody can bind to the Chk1 protein; and detecting the binding. In one alternative embodiment, the sample comprises one or more cells suspected of containing Chk1 protein. In yet another embodiment, the cells contain an abnormal Chk1 protein. In a further embodiment, the cells are selected from the group consisting of human cells and murine cells.

The present invention also provides antibodies capable of recognizing at least a portion of human and/or murine Chk1 protein. In one embodiment, the present invention provides an antibody, wherein the antibody is capable of specifically binding to at least one antigenic determinant on the proteins encoded by an amino acid sequence selected from the group comprising SEQ ID NOS:1, 2, 7, 8, 9, and 10. In one preferred embodiment, the antibody is a polyclonal antibody, while in an alternative embodiment, the antibody is a monoclonal antibody.

The present invention also provides methods for producing antibodies comprising the steps of providing in any order: an antigen comprising at least a portion of Chk1 protein; and an animal having immunocompetent cells; and exposing the animal to the Chk1 protein under conditions such that the immunocompetent cells produce anti-Chk1 antibodies. In one alternative embodiment, the method further comprises the step of harvesting the antibodies. In another alternative embodiment, the antigen comprises at least a portion of Chk1 protein is a fusion protein. In yet another embodiment, the method further comprises the step of fusing the immunocompetent cells with an immortal cell line under conditions such that an hybridoma is produced.

The present invention also provides methods for detection of polynucleotides encoding human and/or murine Chk1 in biological samples. It is not intended that the method be limited to any particular sequence contained within SEQ ID NOS:3 or 4. Indeed, it is contemplated that any sequence be used in the method, including degenerate primers that are based on the sequence of chk1 and that are capable of recognizing at least a portion of the chk1 gene.

In one embodiment, the method comprises the steps of hybridizing a nucleotide comprising at least a portion of the nucleotide of SEQ ID NO:3 to nucleic acid material of a biological sample, thereby forming a hybridization complex; and detecting the hybridization complex, wherein the presence of the complex correlates with the presence of a polynucleotide encoding human Chk1 in the biological sample.

In an alternative embodiment of the method, the biological sample is amplified by the polymerase chain reaction before hybridization. In yet another alternative method, polymerase chain reaction is conducted using primers selected from the group consisting of SEQ ID NOS:5, 6, 12, 13, 14, and 15.

DESCRIPTION OF THE FIGURES

FIG. 1 shows the cDNA sequence of human chk1 (SEQ ID NO:3), as well as the predicted amino acid sequence (SEQ ID NO:1).

FIG. 2 shows the cDNA sequence of murine chk1 (SEQ ID NO:4), as well as the predicted amino acid sequence (SEQ ID NO:2).

DESCRIPTION OF THE INVENTION

Figure 3:
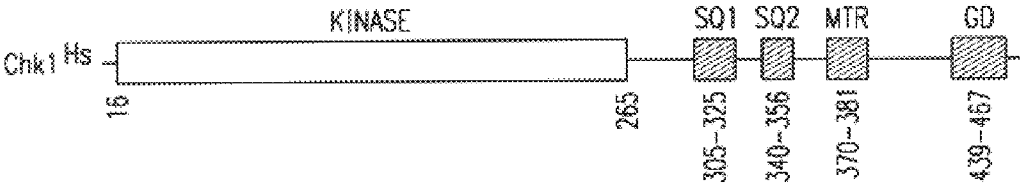
FIG. 3 shows the domain structure of the predicted human Chk1.

The cell cycle comprises a collection of highly ordered processes that lead to the duplication of cells. As cells move through the cell cycle, they undergo several discrete transitions (i.e., an unidirectional change of state in which a cell that was performing one set of processes shifts its activity to perform a different set of processes). Although the mechanism of how these transitions are coordinated to occur at precise times and in a defined order remains unknown, in principle, the ordering of cell cycle events may be accomplished by requiring the next event to physically require the completion of the previous event. This pathway has been referred to as a "substrate-product relationship" (Hartwell and Weinert, Science 246:629 [1989]). However, other research has shown that the predominant mechanism for dependency relies upon positive or negative regulatory circuits.

These regulatory circuits are surveillance mechanisms that monitor the completion of critical cell cycle events, and allow the occurrence of subsequent cell cycle transitions. Two classes of regulatory circuits have been described. "Intrinsic" mechanism act in each cell cycle to order events, while "extrinsic" mechanisms are induced to act only when a defect is detected. Both of these mechanisms may use the same components to enforce cell cycle arrest. These pathways are particularly important, as their loss leads to reduced fidelity of cell cycle events such as chromosome duplication and segregation. Also, such alterations decrease the reproductive fitness of unicellular organisms, and may lead to uncontrolled cellular proliferation and cancer in multi-cellular organisms.

The term "checkpoint" is used to refer to particular subsets of these intrinsic and extrinsic mechanisms. As used herein, a "checkpoint" is a biochemical pathway that ensures dependence of one process upon another process that is otherwise biochemically unrelated. As a null allele in a checkpoint gene results in a loss of this dependency, checkpoints are inhibitory pathways. This definition is broad, and can apply to many situations that occur in multicellular organisms, particularly during development. However, it is often used in reference to control of cell cycle transitions. In preferred embodiments, the term refers to the biochemical pathway that ensures dependency. For example, the DNA-damage checkpoint is the mechanism by which damaged DNA is detected and a signal is generated that arrests cells in the G1 phase of the cell cycle, slows down S phase (i.e., DNA synthesis), arrests cells in the G2 phase, and induces the transcription of repair genes. The position of arrest within the cell cycle varies, depending upon the phase in which the damage is determined. Whether the loss of a checkpoint has an immediate consequence for an organism during a normal cell cycle depends upon the particular pathway involved and the inherent timing of the processes. Thus, timing and checkpoints can act as redundant controls, in order to ensure the proper order of events. Therefore, there are no constraints on whether checkpoints are essential or inducible (extrinsic).

To address the conservation of checkpoint function, a search for human homologs of yeast checkpoint genes was conducted using a degenerate polymerase chain reaction (PCR) strategy. This search identified a human gene very similar to spChk1 (See, FIG. 3). Using hChk1 cDNA (SEQ ID NO:3) as a probe, the mChk1 gene from mouse (SEQ ID NO:4) was isolated. The sequence of the longest human cDNA (1891 bp) predicted a translation product of 476 amino acids with a molecular size of 54 kD (FIG. 3). No in-frame stop codon was found upstream of the first methionine, which is within the Kozak consensus sequence, and is likely to be the bone fide initiation codon because its encoded protein is the same size as that observed in cells (see below). hChk1 was found to be related to a *C. elegans* gene in the database and a *D. melanogaster* gene, grp, with a role in cell cycle control and development (See e.g., FIG. 3). The predicted hChk1 is 29% identical and 44% similar to spChk1, 40% identical and 56% similar to the ceChk1, and 44% identical and 56% similar to dmChk1. Sequence analysis revealed several COOH-terminal domains that are highly conserved in the Chk1 family of kinases (See e.g., FIG. 4).

The chromosomal location of hChk1 was then mapped to 11q24 by fluorescence in situ hybridization. This site is adjacent to the ATM gene at 11q23. This was of interest as ATM is mutated in patients with ataxia telangectasia, a fatal disease characterized by autosomal recessive inheritance, immunological impairment, ataxia related to progressive cerebellar Purkinje cell death, and a high incidence of cancer (See e.g., L. S. Cox and D. P. Lane, Bioessays 17:501 [1995]; Y. Shiloh et al., J. Hum. Genet., 3:116 [1995]; K Savitsky et al., Science 268:1749 [1995]); and K. Savitsky et al., Hum. Mol. Genet., 4:2025 [1995]). Approximately 1% of humans are heterozygotic for ATM defects, and show an increased incidence of cancer (See, M. Swift et al, N. Eng. J. Med., 316:1289 [1987]; and M. Swift et al., N. Eng. J. Med., 325:1831 [1991]).

Figure 5A:
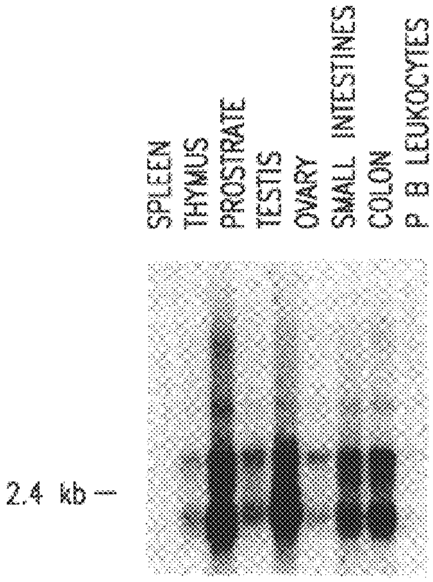
FIG. 5A shows the expression pattern of human Chk1 mRNA in different adult tissues, as determined by Northern analysis.
Figure 5B:
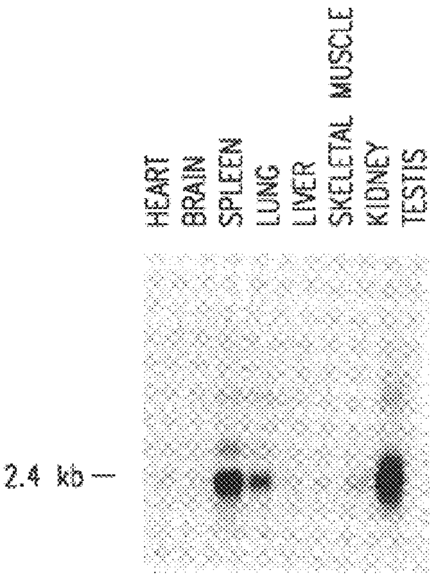
FIG. 5B shows the expression pattern of murine Chk1 mRNA in different adult tissues, as determined by Northern analysis.

Northern blot analysis revealed ubiquitous expression with large amounts of Chk1 expression in human thymus, testis, small intestine and colon (FIG. 5). In this analysis, blots containing the polyadenylated RNA from the indicated tissues were probed with human (FIG. 5A) or mouse (FIG. 5B) chk1 cDNAs. As shown in FIG. 5B, in adult mice, mChk1 was detected in all tissues examined and in large amounts in the testis, spleen, and lung. In addition, mouse embryos revealed ubiquitous expression, with large amounts detected in the brain, liver, kidney, pancreas, intestines, thymus and lung. This was of interest as testis, spleen and thymus also express large amounts of ATM (G. Chen and E. Y. H. P. Lee, J. Biol. Chem., 271:33693 [1996]; N. D. Lakin et al., Oncogene 13:2707 [1996]).

Figure 6:
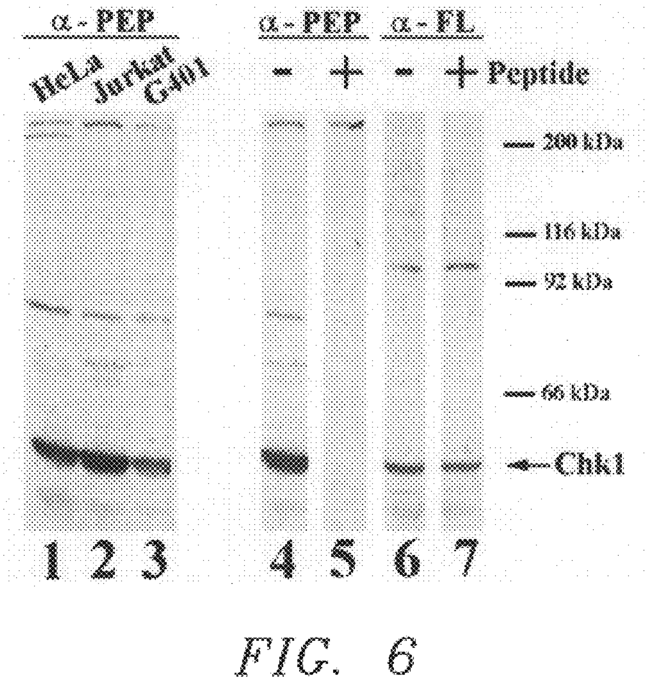
FIG. 6 shows the reactivity of a 54 kD protein from different cell lines, with purifed antibodies directed to a peptide (anti-PEP), or full-length Chk1 protein anti-FL).

Affinity purified antibodies to hChk1 protein (GST fusion hChk1 protein) made in baculovirus (anti-FL) or to its COOH-terminal 15 amino acids (anti-PEP) recognized a 54-kD protein (FIG. 6) that comigrates with hChk1 expressed in baculovirus. As shown in this Figure, the anti-PEP, but not anti-FL signal is competed by addition of excess peptide, indicating that the two sera are recognizing different hChk1 epitopes, further confirming identity of the 54-kD band as endogenous hChk1. A 70 kD protein was also specifically recognized by anti-PEP.

When mChk1 was expressed from the cytomegalovirus (CMV) promoter in baby hamster kidney (BKH) cells, a 54 kD nuclear protein was detected only in transfected cells using antibodies directed against the C-terminal peptide of mChk1. This exogenous mChk1 was found to comigrate with endogenous mChk1 from mouse lung tissue.

Figure 7A:
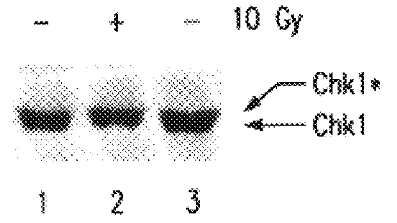
FIG. 7A shows that Chk1 is modified in response to DNA damage in HeLa cells.
Figure 7B:
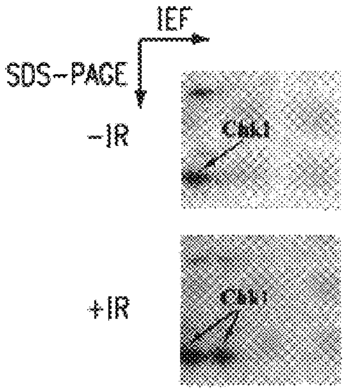
FIG. 7B shows that Chk1 in modified in response to DNA damage in Jurkat cells.

To determine whether hChk1 is modified in response to DNA damage like spChk1, hChk1 protein in extracts from cells treated with ionizing radiation was examined. hChk from extracts obtained from damaged cells showed a minor but reproducible reduction in mobility compared to hChk1 from untreated cells (See, FIG. 7). The mobility alteration observed in response to DNA damage for spChk1 was also slight, as previously reported (See e.g., N. C. Walworth et al., Nature 363:368 [1993]; Al-Khodairy et al., Mol. Biol. Cell 5:147 [1994]; and N. C. Walworth and R. Bernards, Science 271:353 [1996]). This modification was confirmed by 2-dimensional gel analysis, which clearly demonstrated the generation of a more negatively charged hChk1 species 2 hours after γ-irradiation (See, FIG. 7). These results indicate that like spChk1, hChk1 may participate in transduction of the DNA damage signal. Indirect immunofluorescence revealed that hChk1 is localized to the nucleus in a punctate staining pattern, similar to that observed for ATM (See, G. Chen and E. Y. H. P. Lee, J. Biol. Chem., 271:33693 [1996]; and N. D. Lakin et al., Oncogene 13:2702 [1996]). mChk1 expressed in BHK cells confirmed the nuclear localization.

To test for the ability of hChk1 to regulate the cell cycle, hChk1 or hChk1 (D130A) (a catalytically inactive mutant), were transfected under the control of the CMV promoter, or the CMV vector alone into HeLa cells treated with and without 6 Gy of ionizing radiation. No perturbation of the cell cycle by either kinase relative to vector alone was observed, suggesting that overproduction alone was insufficient to deregulate the system.

Tyrosine phosphorylation of Cdc2 has been implicated in cell cycle arrest in response to DNA damage and replication blocks in both *S. pombe* (T. Enoch and P. Nurse, Cell 60:665 [1990]) and humans (P. Jin et al., J. Cell Biol., 134:963 [1996]). In *S. pombe,* Cdc2 mutants that cannot be phosphorylated on tyrosine display an inability to arrest the cell cycle in response to blockade of DNA replication. Although it was originally thought that the DNA damage checkpoint did not operate through tyrosine phosphorylation, recent experiments have shown that tyrosine phosphorylation is required for *S. pombe* cells to arrest in response to DNA damage (P. Jin et al., J. Cell Biol., 134:963 [1996]). While it is now clear that tyrosine phosphorylation is required for proper checkpoint control, the experiments implicating tyrosine phosphorylation in this pathway do not distinguish between a regulatory role in which tyrosine phosphorylation rates are manipulated by the checkpoint pathways, or a passive role in which tyrosine phosphorylation is required to allow cell cycle arrest, but is not the actual target of the checkpoint pathway (S. Elledge, Science 274:1664 [1996]; and D. J. Lew and S. Kornbluth, Curr. Opin. Cell. Biol., 8:795 [1996]).

Figure 8A:
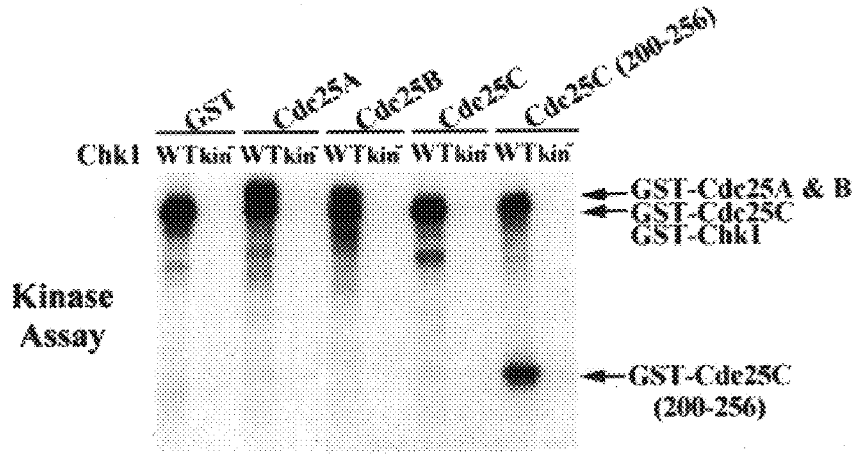
FIG. 8A is an autoradiograph showing radiolabeled phosphate incorporation due to phosphorylation of Chk1, Cdc25A, Cdc25B, and Cdc25C.

To address this issue, the ability of hChk1 to phosphorylate key regulators of Cdk tyrosine phosphorylation was examined. For these experiments, the Cdc25 dual-specificity phosphatases, hCdc25A, hCdc25B, and hCdc25C were analyzed. These regulators were chosen for several reasons. First, overproduction of hCdk4 mutants in which the inhibitory tyrosine is changed to phenylalanine abrogates G1 arrest in response to UV light (Y. Terada et al., Nature 376:358 [1995]). Secondly, the UV-sensitivity of $chk1^-$ mutants in *S. pombe* is suppressed by inactivating cdc25 with a Ts (i.e., temperature sensitive) mutation (N. C. Walworth et al., Nature 363:368 [1993]). Finally, in *S. pombe* wee1mik1 mutants, DNA damage still causes a partial cell cycle delay that could be due to regulation of spCdc25 activity. GST-hChk1 and GST-hChk1 (D130A) were introduced into baculovirus, purified from baculovirus-infected insect cells, and incubated with GST-hCdc25A, GST-hCdc25B, and GST-hCdc25C, as described in Example 5. GST-hChk1 phosphorylated all three Cdc25 proteins, but GST alone did not (See, FIG. 8). Although GST-hCdc25C co-migrated with GST-hChk1 (which autophosphorylates), increased phosphorylation was observed at that position relative to phosphorylation in the presence of kinase alone, and phosphorylation of a GST-hCdc25C breakdown product was visible. In separate experiments using a $His_6$-tagged hChk1 derivative, there was clear phosphorylation of GST-hCdc25C (FIG. 9). A catalytically inactive mutant failed to phosphorylate itself or any of the Cdc25 proteins (See, FIG. 8).

Protein kinases often form complexes with their substrates. To examine determine whether this occurs with for hChk1 and the Cdc25 proteins, GST-hCdc25 proteins on glutathione beads were incubated together with baculovirus extracts expressing $His_6$-tagged hChk1, and precipitated. GST-hCdc25A, GST-hCdc25B and GST-hCdc25C, each specifically bound hChk1, while GST alone did not (See, FIG. 10). Furthermore, two other GST fusion proteins, GST-Dun1 and GST-Skp1, all failed to bind hChk1. These results indicate that Cdc25 can form complexes with hChk.

Figure 11:
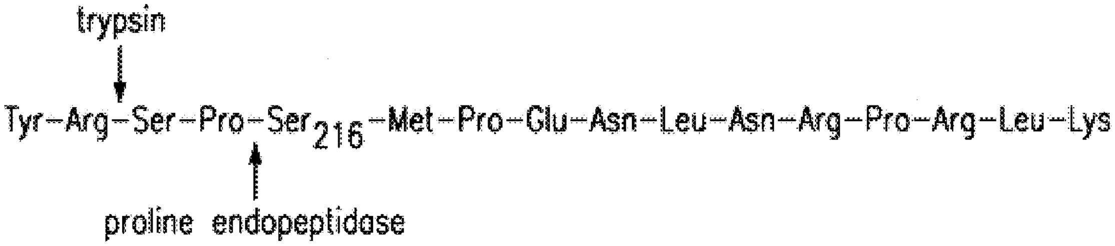
FIG. 11 shows the proteolytic sites surrounding serine 216 on Cdc25C
Figure 12A:
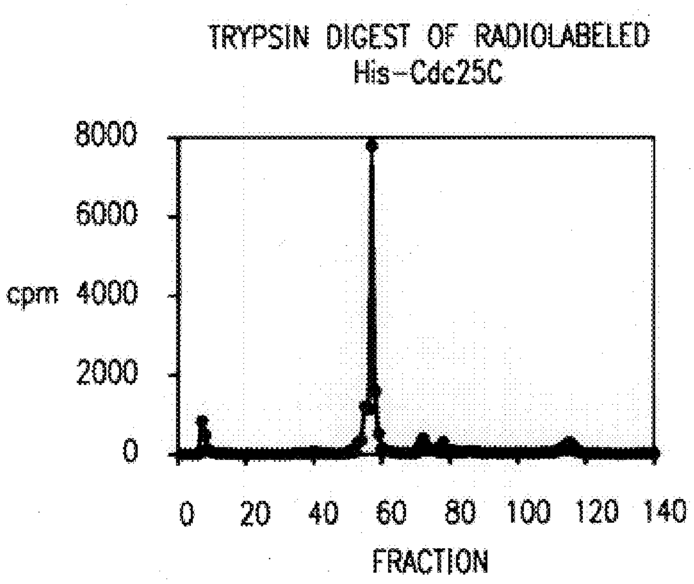
FIG. 12A shows the results of mapping of the phosphorylation site on Cdc25C by Chk1 by proteolytic cleavage and sequencing of phosphorylated Cdc25C, as resolved by HPLC.
Figure 12B:
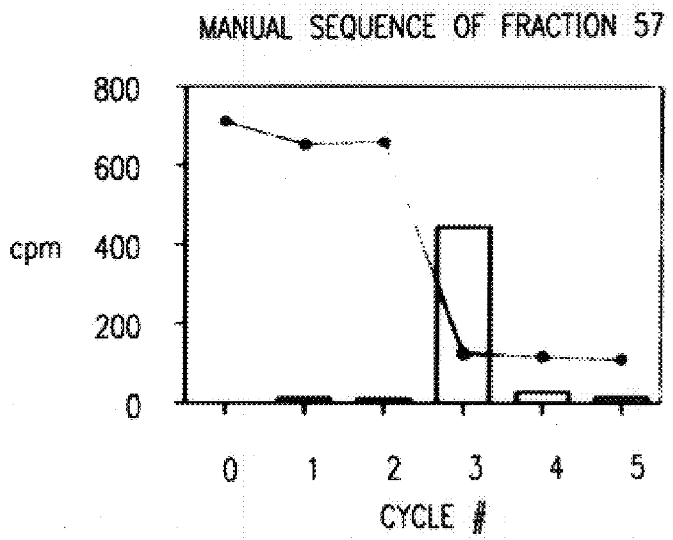
FIG. 12B provides identification of phosphorylated residue by manual Edman degradation of tryptic peptide present in fraction 57 shown in FIG. 12A.

To establish the significance of the Cdc25 phosphorylation, the site of hChk1 phosphorylation on Cdc25C was mapped. It was determined that $Ser^{216}$ is the main site of phosphorylation of hCdc25C in vivo. hChk1 phosphorylated a 56 amino acid region of the hCdc25C protein fused to GST, but not GST alone (FIGS. 8 and 9). This 56 amino acid motif contains four possible sites of phosphorylation. Peptide analysis of proteolytic fragments of full length $His_6$-hCdc25C phosphorylated with GSt-hChk1 revealed a single phosphorylated tryptic peptide by high pressure liquid chromatography. Edman degradation of this peptide indicated release of radioactivity in the third cycle (FIG. 12B). Further degradation of this tryptic fragment with proline endopeptidase resulted in production of a peptide that released radioactivity in the first cycle. The $Serine^{216}$ residue is the only site on hCdc25C that is consistent with this phosphorylation pattern (FIG. 11). To confirm this, the Cdc25C S216A mutation in GST-Cdc25C and Cdc25C(200–256) were constructed. It was determined that both were poor substrates for hChk1, confirming that $Serine^{216}$ is the site phosphorylation (FIG. 9). Serine 216 is also phosphorylated by spChk1, demonstrating phylogenetic conservation of this regulatory relationship.

The present invention provides evidence that the Chk1 kinase family is conserved throughout eukaryotic evolution and that hChk1, like its *S pombe* counterpart, is modified in response to DNA damage. This, together with the fact that ATM-related kinases are conserved members of checkpoint pathways and act upstream of chk1 in *S. pombe,* suggests that this entire checkpoint pathway may be conserved in all eukaryotes. Nonetheless, the present invention provides the first mammalian Chk1 sequences.

hChk1 directly phosphorylates a regulator of Cdc2 tyrosine phosphorylation, hCdc25C, on a physiologically significant residue, $Serine^{216}$. In addition, overexpression of the hCdc25C S216A protein reduces the ability of cells to arrest in G2 in response to DNA damage, as observed previously for the Cdc2AF mutants. However, the overexpression studies alone do not prove that the DNA damage checkpoint pathway operates through tyrosine phosphorylation, because hyperactive Cdc2 may be able to bypass checkpoint control. Nonetheless, in combination with the fact that this inhibitory serine is directly phosphorylated by the DNA damage-responsive checkpoint kinase hChk1, these results strongly imply that DNA damage regulates the G2-to-mitosis transition through control of Cdc2 tyrosine phosphorylation. These results suggest a model whereby in response to DNA damage, hChk1 phosphorylates hCdc25C on $Serine^{216}$, leading to binding of 14-3-3 protein and inhibition of Cdc25C's ability to dephosphorylate and activate Cdc2. This model does not preclude a role for other cell cycle regulators such as Wee1 in the damage response. Although an understanding of the mechanism is not necessary in order to use the present invention, the facts that hChk1 phosphorylated hCdc25A and hCdc25B, and that $Serine^{216}$ is conserved among these Cdc25 proteins, suggests that hChk1 may regulate other DNA damage checkpoints, such as those controlling the G1 to S phase transition, through a similar mechanism.

Definitions

To facilitate understanding of the invention, a number of terms are defined below.

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

A "composition comprising a given polynucleotide sequence" as used herein refers broadly to any composition containing the given polynucleotide sequence. The composition may comprise an aqueous solution. Compositions comprising polynucleotide sequences encoding human or murine Chk1 (SEQ ID NOS:3 and 4) or fragments thereof, may be employed as hybridization probes. In this case, the human and murine chk1-encoding polynucleotide sequences are typically employed in an aqueous solution containing salts (e.g., NaCl), detergents (e.g., SDS) and other components (e.g., Denhardt's solution, dry milk, salmon sperm DNA, etc.).

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid," as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al., Anticancer Drug Des. 8:53–63 [1993]).

Chk1 as used herein, refers to the amino acid sequences of substantially purified Chk1 obtained from any species, particularly mammalian, including bovine, ovine, porcine, murine, equine, and human, from any source whether natural, synthetic, semi-synthetic, or recombinant. In particularly preferred embodiments, Chk1 is human or murine.

"Consensus," as used herein, refers to a nucleic acid sequence which has been resequenced to resolve uncalled bases, or which has been extended using any suitable method known in the art, in the 5' and/or the 3' direction and resequenced, or which has been assembled from the overlapping sequences of more than one clone using any suitable method known in the art, or which has been both extended and assembled.

A "variant" of human or murine Chk1, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of a glycine with a tryptophan). Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion," as used herein, refers to a change in either amino acid or nucleotide sequence in which one or more amino acid or nucleotide residues, respectively, are absent.

An "insertion" or "addition," as used herein, refers to a change in an amino acid or nucleotide sequence resulting in the addition of one or more amino acid or nucleotide residues, respectively, as compared to the naturally occurring molecule.

A "substitution," as used herein, refers to the replacement of one or more amino acids or nucleotides by different amino acids or nucleotides, respectively.

The term "biologically active," as used herein, refers to a protein having structural, regulatory, or biochemical functions of a naturally occurring molecule. Likewise, "immunologically active" refers to the capability of the natural, recombinant, or synthetic human or murine Chk1, or any oligopeptide thereof, to induce a specific immune response in appropriate animals or cells and to bind with specific antibodies.

The term "modulate," as used herein, refers to a change or an alteration in the biological activity of human or murine Chk1. Modulation may be an increase or a decrease in protein activity, a change in binding characteristics, or any other change in the biological, functional, or immunological properties of human or murine Chk1.

The term "mimetic," as used herein, refers to a molecule, the structure of which is developed from knowledge of the structure of Chk1, or portions thereof and, as such, is able to effect some or all of the actions of human or murine Chk1-like molecules.

The term "derivative," as used herein, refers to the chemical modification of a nucleic acid encoding human or murine Chk1, or the encoded human or murine Chk1 protein. Illustrative of such modifications would be replacement of hydrogen by an alkyl, acyl, or amino group. A nucleic acid derivative would encode a polypeptide which retains essential biological characteristics of the natural molecule.

The term "substantially purified," as used herein, refers to nucleic or amino acid sequences that are removed from their natural environment, isolated or separated, and are at least 60% free, preferably 75% free, and most preferably 90% free from other components with which they are naturally associated.

The term "hybridization," as used herein, refers to any process by which a strand of nucleic acid binds with a complementary strand through base pairing. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m$=81.5+0.41(% G+C), when a nucleic acid is in aqueous solution at 1 M NaCl (see e.g, Anderson and Young, *Quantitative Filter Hybridization, in Nucleic Acid Hybridization* (1985). Other references include more sophisticated computations which take structural as well as sequence characteristics into account for the calculation of $T_m$.

The term "hybridization complex," as used herein, refers to a complex formed between two nucleic acid sequences by virtue of the formation of hydrogen binds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity," as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology," as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence. When used in reference to a single-stranded nucleic acid sequence, the term "substantially homologous" refers to any probe which can hybridize (i.e., it is the complement of) the single-stranded nucleic acid sequence under conditions of low stringency as described.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions. As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

Low stringency conditions comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent (50×Denhardt's contains per 500 ml: 5 g Ficoll (Type 400, Pharamcia), 5 g BSA[Fraction V; Sigma]) and 100 μg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions which promote hybridization under conditions of high stringency (e.g., increasing the temperature of the hybridization and/or wash steps, the use of formamide in the hybridization solution, etc.).

The term "antisense," as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term also is used in reference to RNA sequences which are complementary to a specific RNA sequence (e.g, mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter which permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (–) (i.e., "negative") is sometimes used in reference to the antisense strand, with the designation (+) sometimes used in reference to the sense (i.e., "positive") strand.

A gene may produce multiple RNA species which are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

The term "portion," as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:3" encompasses the full-length human Chk1, and fragments thereof.

"Transformation," as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Thus, the term "stable transfection" or "stably transfected" refers to the introduction and integration of foreign DNA into the genome of the transfected cell. The term "stable transfectant" refers to a cell which has stably integrated foreign DNA into the genomic DNA. The term also encompasses cells which transiently express the inserted DNA or RNA for limited periods of time. Thus, the term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

The term "antigenic determinant," as used herein, refers to that portion of a molecule (i.e., an antigen) that makes contact with a particular antibody (i.e., an epitope). When a protein or fragment of a protein is used to immunize a host animal (e.g., an "immunocompent" animal with "immunocompetent cells"), numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding," as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample," as used herein, is used in its broadest sense. The term encompasses biological sample(s) suspected of containing nucleic acid encoding human or murine Chk1 or fragments thereof, and may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide," as used herein, indicates that the detection of the presence of ribonucleic acid that is similar to SEQ ID NO:3 or 4, by Northern analysis is indicative of the presence of mRNA encoding human or murine Chk1, in a sample and thereby correlates with expression of the transcript from the polynucleotide encoding the protein.

"Alterations" in the polynucleotide of SEQ ID NO:3 or 4, as used herein, comprise any alteration in the sequence of polynucleotides encoding human or murine Chk1, respectively, including deletions, insertions, and point mutations that may be detected using hybridization assays. Included within this definition is the detection of alterations to the genomic DNA sequence which encodes human Chk1 (e.g., by alterations in the pattern of restriction fragment length polymorphisms capable of hybridizing to SEQ ID NO:1), the inability of a selected fragment of SEQ ID NO:3 to hybridize to a sample of genomic DNA (e.g., using allele-specific oligonucleotide probes), and improper or unexpected hybridization, such as hybridization to a locus other than the normal chromosomal locus for the polynucleotide sequence encoding human Chk1 (e.g., using fluorescent in situ hybridization [FISH] to metaphase chromosomes spreads).

As used herein, the term "antibody" (or "immunoglobulin"), refers to intact molecules as well as fragments thereof, such as Fa, $F(ab')_2$, and Fv, which are capable of binding the epitopic determinant. Antibodies that bind human or murine Chk1 polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody," as used herein, refers to antibody molecules in which amino acids have been replaced in the non-antigen binding regions in order to more closely resemble a human antibody, while still retaining the original binding ability.

As used herein, the term "poly$A^+$ RNA" refers to RNA molecules having a stretch of adenine nucleotides at the 3' end. This polyadenine stretch is also referred to as a "poly-A tail". Eukaryotic mRNA molecules contain poly-A tails and are referred to as poly$A^+$ RNA.

As used herein, the term "fusion protein" refers to a chimeric protein containing the protein of interest (i.e., mouse or human chk1 and fragments thereof) joined to an exogenous protein fragment (the fusion partner which consists of a non-chk1 protein). The fusion partner may enhance solubility of the chk1 protein as expressed in a host cell, may provide an affinity tag to allow purification of the recombinant fusion protein from the host cell or culture supernatant, or both. If desired, the fusion protein may be removed from the protein of interest (i.e., chk1 protein or fragments thereof) by a variety of enzymatic or chemical means known to the art.

As used herein, the term "affinity tag" refers to such structures as a "poly-histidine tract" or "poly-histidine tag," or any other structure or compound which facilitates the purification of a recombinant fusion protein from a host cell, host cell culture supernatant, or both. As used herein, the term "flag tag" refers to short polypeptide marker sequence useful for recombinant protein identification and purification.

As used herein, the terms "poly-histidine tract" and "poly-histidine tag," when used in reference to a fusion protein refers to the presence of two to ten histidine residues at either the amino- or carboxy-terminus of a protein of interest. A poly-histidine tract of six to ten residues is preferred. The poly-histidine tract is also defined functionally as being a number of consecutive histidine residues added to the protein of interest which allows the affinity purification of the resulting fusion protein on a nickel-chelate or IDA column.

As used herein, the term "chimeric protein" refers to two or more coding sequences obtained from different genes, that have been cloned together and that, after translation, act as a single polypeptide sequence. Chimeric proteins are also referred to as "hybrid proteins." As used herein, the term "chimeric protein" refers to coding sequences that are obtained from different species of organisms, as well as coding sequences that are obtained from the same species of organisms.

As used herein, the term "protein of interest" refers to the protein whose expression is desired within the fusion protein. In a fusion protein, the protein of interest will be joined or fused with another protein or protein domain, the fusion partner, to allow for enhanced stability of the protein of interest and/or ease of purification of the fusion protein.

As used herein, the term "abnormal Chk1 protein" refers to Chk1 that lacks function (i.e., does not function as Chk1 protein in normal cells), or is not recognized by sequences encoding full-length functional Chk1 protein.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

As used herein, the term "selectable marker" refers to the use of a gene which encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity which can be detected in any eukaryotic cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene which is used in conjunction with $tk^-$ cell lines, the CAD gene which is used in conjunction with CAD-deficient cells and the mammalian hypoxanthine-guanine phosphoribosyl transferase (hprt) gene which is used in conjunction with $hprt^-$ cell lines. A review of the use of selectable markers in mammalian cell lines is provided in Sambrook, J. et al., *Molecular Cloning: A Laboratory Manual,* 2nd ed., Cold Spring Harbor Laboratory Press, New York (1989) pp. 16.9–16.15.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U. S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}P$-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (M. Chamberlin et al., Nature 228:227 [1970]). In the case of T4 DNA ligase, the enzyme will not ligate the two oligonucleotides where there is a mismatch between the oligonucleotide substrate and the template at the ligation junction (D. Y. Wu and R. B. Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology,* Stockton Press [1989]).

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription (T. Maniatis et al., Science 236:1237 [1987]). Promoter and enhancer elements have been isolated from a variety of eukaryotic sources including genes in yeast, insect and mammalian cells and viruses (analogous control elements, i.e., promoters, are also found in prokaryote). The selection of a particular promoter and enhancer depends on what cell type is to be used to express the protein of interest. Some eukaryotic promoters and enhancers have a broad host range while others are functional in a limited subset of cell types (for review see, S. D. Voss et al., Trends Biochem. Sci., 11:287 [1986]; and T. Maniatis et al., supra). For example, the SV40 early gene enhancer is very active in a wide variety of cell types from many mammalian species and has been widely used for the expression of proteins in mammalian cells (R. Dijkema et al., EMBO J. 4:761 [1985]). Two other examples of promoter/enhancer elements active in a broad range of mammalian cell types are those from the human elongation factor 1α gene (T. Uetsuki et al., J. Biol. Chem., 264:5791 [1989]; D. W. Kim et al., Gene 91:217 [1990]; and S. Mizushima and S. Nagata, Nuc. Acids. Res., 18:5322 [1990]) and the long terminal repeats of the Rous sarcoma virus (C. M. Gorman et al., Proc. Natl. Acad. Sci. USA 79:6777 [1982]) and the human cytomegalovirus (M. Boshart et al, Cell 41:521 [1985]).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

The presence of "splicing signals" on an expression vector often results in higher levels of expression of the recombinant transcript. Splicing signals mediate the removal of introns from the primary RNA transcript and consist of a splice donor and acceptor site (J. Sambrook et al., *Molecular Cloning: A Laboratory Manual,* 2nd ed., Cold Spring Harbor Laboratory Press, New York [1989], pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is one which is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (J. Sambrook, supra, at 16.6–16.7).

Eucaryotic expression vectors may also contain "viral replicons "or "viral origins of replication." Viral replicons are viral DNA sequences which allow for the extrachromosomal replication of a vector in a host cell expressing the appropriate replication factors. Vectors which contain either the SV40 or polyoma virus origin of replication replicate to high copy number (up to $10^4$ copies/cell) in cells that express the appropriate viral T antigen. Vectors which contain the replicons from bovine papillomavirus or Epstein-Barr virus replicate extrachromosomally at low copy number (~100 copies/cell).

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "calcium phosphate co-precipitation" refers to a technique for the introduction of nucleic acids into a cell. The uptake of nucleic acids by cells is enhanced when the nucleic acid is presented as a calcium phosphate-nucleic acid coprecipitate. The original technique of Graham and van der Eb (Graham and van der Eb, Virol., 52:456 [1973]), has been modified by several groups to optimize conditions for particular types of cells. The art is well aware of these numerous modifications.

The term "Southern blot" refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. *Molecular Cloning: A Laboratory Manual,* Cold Spring Harbor Press, NY, pp 9.31–9.58 [1989]).

The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, J. et al., supra, pp 7.39–7.52 [1989]).

The term "YIp plasmid" refers to yeast integrating plasmids which contain selectable yeast genes but lack sequences which allow for the autonomous replication of the plasmid in a yeast cell. Transformation of the host yeast cell occurs by integration of the YIp plasmid into the yeast genome. This integration occurs by recombination between yeast sequences present on the YIp plasmid and homologous sequences present in the genome.

The term "prototrophic" or "prototrophy" refers to an organism that can survive growth under conditions where one or more essential nutrients are lacking in the growth medium. For example, if a yeast cell is transformed to histidine prototrophy, this means that the yeast cell now contains gene sequences encoding the enzyme necessary for the production of the amino acid histidine; therefore, the transformed yeast cell does not require the presence of histidine in the growth medium.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNA s which encode a multitude of proteins. However, isolated nucleic acid encoding a mammalian Chk1 protein includes, by way of example, such nucleic acid in cells ordinarily expressing a Chk1 protein where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

As used herein, a "portion of a chromosome" refers to a discrete section of the chromosome. Chromosomes are divided into sites or sections by cytogenetists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA which is produced by transcription of genes located on a chromosome (e.g., hnRNA and mRNA) and cDNA copies of the RNA transcribed from the DNA located on a chromosome. Sequences associated with a chromosome may be detected by numerous techniques including probing of Southern and Northern blots and in situ hybridization to RNA, DNA or metaphase chromosomes with probes containing sequences homologous to the nucleic acids in the above listed preparations.

As used herein the term "coding region" when used in reference to structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes which encode products which control the expression of other genes (e.g., transcription factors).

As used herein, the term "gene" means the deoxyribonucleotide sequences comprising the coding region of a structural gene and the including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences; these sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

As used herein, the term "purified" or "to purify" refers to the removal of contaminants from a sample. For example, anti-chk1 antibodies are purified by removal of contaminating non-immunoglobulin proteins; they are also purified by the removal of immunoglobulin that does not bind chk1. The removal of non-immunoglobulin proteins and/or the removal of immunoglobulins that do not bind chk1 results in an increase in the percent of chk1-reactive immunoglobulins in the sample. In another example, recombinant chk1 polypeptides are expressed in bacterial host cells and the polypeptides are purified by the removal of host cell proteins; the percent of recombinant chk1 polypeptides is thereby increased in the sample.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein, the term "chk1 protein" or "chk1 protein sequence" refers to a protein which is encoded by a chk1 gene sequence or to a protein.

As used herein, the term "non-chk1 protein" or "non-chk1 protein sequence" refers to that portion of a fusion protein which comprises a protein or protein sequence which is not derived from a chk1 protein.

Experimental

The following examples are provided in order to demonstrate and further illustrate certain preferred embodiments and aspects of the present invention and are not to be construed as limiting the scope thereof.

In the experimental disclosure which follows, the following abbreviations apply: h (human); sc (*Saccharomyces cerevisiae*); sp (*Schizosaccharomyces pombe*); ce (*Caenhorrhabditis elegans*); dm (*Drosophila melanogaster*); ° C. (degrees Centigrade); rpm (revolutions per minute); BSA (bovine serum albumin); CFA (complete Freund's adjuvant); IFA (incomplete Freund's adjuvant); IgG (immunoglobulin G); IM (intramuscular); IP (intraperitoneal); IV (intravenous or intravascular); SC (subcutaneous); $H_2O$ (water); HCl (hydrochloric acid); aa (amino acid); bp (base pair); kb (kilobase pair); kD (kilodaltons); gm (grams); μg (micrograms); mg (milligrams); ng (nanograms); μl (microliters); ml (milliliters); mm (millimeters); nm (nanometers); μm (micrometer); M (molar); mM (millimolar); MW (molecular weight); sec (seconds); min(s) (minute/minutes); hr(s) (hour/hours); $MgCl_2$ (magnesium chloride); NaCl (sodium chloride); $OD_{280}$ (optical density at 280 nm); $OD_{600}$ (optical density at 600 nm); PAGE (polyacrylamide gel electrophoresis); PBS (phosphate buffered saline [150 mM NaCl, 10 mM sodium phosphate buffer, pH 7.2]); PEG (polyethylene glycol); PMSF (phenylmethylsulfonyl fluoride); SDS (sodium dodecyl sulfate); Tris (tris (hydroxymethyl)aminomethane); w/v (weight to volume); v/v (volume to volume); Amersham (Amersham Life Science, Inc. Arlington Heights, Ill.); ICN (ICN Pharmaceuticals, Inc., Costa Mesa, Calif.); Amicon (Amicon, Inc., Beverly, Mass.); ATCC (American Type Culture Collection, Rockville, Md.); Becton Dickinson (Becton Dickinson Labware, Lincoln Park, N.J.); BioRad (BioRad, Richmond, Calif.); Clontech (CLONTECH Laboratories, Palo Alto, Calif.); Difco (Difco Laboratories, Detroit, Mich.); GIBCO BRL or Gibco BRL (Life Technologies, Inc., Gaithersburg, Md.); Invitrogen (Invitrogen Corp., San Deigo, Calif.); Kodak (Eastman Kodak Co., New Haven, Conn.); New England Biolabs (New England Biolabs, Inc., Beverly, Mass.); Novagen (Novagen, Inc., Madison, Wis.); Pharmacia (Pharmacia, Inc., Piscataway, N.J.); Sigma (Sigma Chemical Co., St. Louis, Mo.); Sorvall (Sorvall Instruments, a subsidary of DuPont Co., Biotechnology Systems, Wilmington, Del.); Stratagene (Stratagene Cloning Systems, La Jolla, Calif.); Whatman (Whatman LabSales, Hillsboro, Oreg.); Bethyl Laboratories (Bethyl Laboratories, Montgomery, Tex.); and Zeiss (Carl Zeiss, Inc., Thornwood, N.Y.).

Unless otherwise indicated, all restriction enzymes were obtained from New England BioLabs and were used according to the manufacturer's instructions; all oligonucleotide primers, adapter and linkers were synthesized using standard methodologies on an ABI DNA synthesizer. All chemicals were obtained from Sigma unless otherwise indicated.

EXAMPLE 1

Human and Murine Chk1

In this Example, human and murine checkpoint genes were identified by searching for homologs of yeast checkpoint genes. In the experiments to identify the human homolog, degenerate PCR primers to conserved motifs in the kinase domains of spChk1 were used to screen a human B cell library by PCR, as known in the art.

A DNA fragment containing the ORF for the hChk1 gene was obtained using the polymerase chain reaction (PCR) as follows. The DNA was obtained from human peripheral blood lymphocytes. Gel-purified degenerate primers used in the reaction were 5'-GGNGGNGAGT/CT/CTNATGGAT/CTT-3' (SEQ ID NO:5) and 5'-TTGGACAGGCCAAAGTC-3' (SEQ ID NO:6). The reaction conditions comprised the following steps: denaturation at 95° C. for 5 minutes, 80° C. for 1 minutes, during which Taq was added, and thirty cycles of 95° C. for 30 seconds; 52° C. for 30 seconds; and 72° C. for 2 minutes.

Four of 35 clones showed similarity to spChk1, and one clone was used to probe $2\times10^5$ plaques from a λACT human B cell cDNA library. This probe was also used in subsequent experiments (it is referred to as the "PCR probe"). A partial sequence of this probe was determined and is shown below:

```
(5'gggggggagctgtttgaccgaatagagccagacataggcatgcctgaaccagatgctcagagattcttccatca
actcatgggaggggtggtttatctgcatggtatggaataactcacagggatattaaaccagaaaatcttctgttggaag
aaagggataacctcaaaatctcagactttggc-3')(SEQ ID NO:11).
```

The library was constructed using methods known in the art (See, T. Durfee et al., Genes Develop., 7:555–569 [1993]), and deposited with the ATCC (ATCC Accession No. ATC 87003). The library was screened by hybridizing DNA present on filters with radiolabeled PCR probe (described above) in Hybridization Solution I (48% formamide, 5×SSC, 20 mM Tris-Cl, pH 7.6, ×Denhardt's solution, 10% dextran sulfate, and 0.1% SDS) at 42° C. overnight. The filters were washed three times in low stringency wash (2×SSC/0.1% SDS) for 10 minutes at room temperature, and twice in high stringency wash (0.2×SSC/ 0.1% SDS) at 65° C., and then exposed for autoradiography.

The plaques showing hybridization to probe were isolated and used to infect a bacterial strain expressing the Cre enzyme. The recombinant plasmids containing the cDNA inserts were purified and screened by Southern analyses using the PCR-generated probe described and used above. Probing of this library resulted in the identification of two hchk1 cDNAs. Neither of these clones were complete, as the longest cDNA was lacking a few base pairs near the 5' end. The full-length clone was constructed by ligating the 5' end of the short clone onto the longer cDNA clone to produce the sequence shown in FIG. 1 (SEQ ID NO:3).

Once the human homolog was identified, human Chk1 cDNA was used to isolate the murine chk1 (mChk1). A mouse T cell cDNA library (ATCC Accession No. ATC 87291) was screened using a NotI-ClaI fragment from the hchk1 cDNA as a probe as described above for the human library screen, with the exception being that the high stringency wash was conducted at 42° C. In addition, a genomic clone was isolated from a mouse ES cell library that contains chk1. This clone was found to contain the chk1 exons (i.e., the sequence provided in SEQ ID NO:4).

The sequence of the longest human cDNA (1891 base pairs) predicted a translation product of 476 amino acids, with an approximate size of 54 kD. No in-frame stop codon was found upstream of the first methionine, which is located with the Kozak consensus sequence (See, Kozak, Cell 44:283 [1986]), and is likely to be the initiation codon, as its encoded protein is the same size as that observed in cells (as discussed below). FIG. 1 shows the sequence of the cDNA encoding human chk1 (SEQ ID NO:1)(Genbank Accession No. AF016582), as well as the predicted amino acid sequence for the human Chk1 protein (SEQ ID NO:1). FIG. 2 shows the cDNA sequence of murine chk1 (SEQ ID NO:4)(Genbank Accession No. AF016583), as well as the predicted amino acid sequence for the murine Chk1 protein (SEQ ID NO:2).

Figure 4:
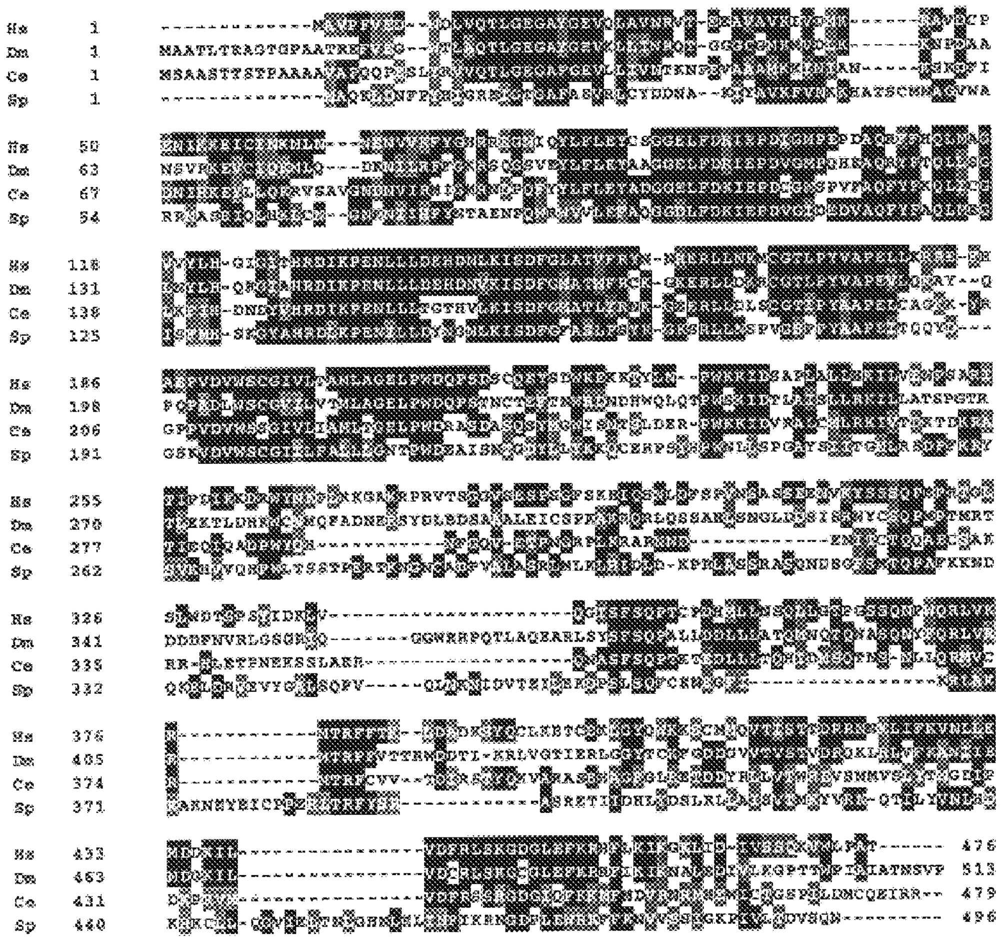
FIG. 4 shows the alignment of human, *D. melanogaster, C. elegans,* and *S. pombe* Chk1 homologs.

The human Chk1 gene is likely to be related to a *Caenorabditis elegans* gene and the *Drosophila melanogaster* gene grp. However, during this experimental work, it was determined that the database DNA sequence for ceChk1 has a likely frame shift in the COOH-terminus. FIG. 3 shows the domain structure of the predicted human Chk1 (hChk1) protein. In this Figure, the black boxes indicate regions of highest conservation. FIG. 4 shows the alignment of Chk1 homologs. In this Figure, amino acid identities are shown as black boxes, and conservative changes are shown as shaded boxes. In this Figure, "Hs" indicates *Homo sapiens, "Sp"* indicates *S. pombe, "Ce"* indicates *C. elegans,* and "Dm" indicates *D. melanogaster.* In this Figure, the human sequence is SEQ ID NO:7, the *D. melanogaster* sequence is SEQ ID NO:8, the *C. elegans* sequence is SEQ ID NO:9, and the *S. pombe* sequence is SEQ ID NO:10.

The predicted hChk1 protein was found to be 29% identical and 44% similar to spChk1, 40% identical and 56% similar to the ceChk1, and 44% identical and 56% similar to dmChk1. Sequence analysis revealed several COOH-terminal domains that appear to be highly conserved in the Chk1 family of kinases.

EXAMPLE 2

Mapping of Chk1 and Its Expression

In this Example, Northern analysis of hChk1 and murine hChk1 was used to identify tissues that express Chk1. In addition, the chromosomal location of Chk1 was mapped to 11q24, by fluorescence in situ hybridization (FISH), as known in the art.

In the in situ hybridization experiments, tissues from adult mice, and murine embryos from day 15.5 post coitum (p.c.) were examined. Embryos or tissues were collected and fixed in 4% paraformaldehyde, embedded in paraffin and sectioned on a microtome (Zeiss) at 5 $\mu$. Specimens were hybridized with α-35S-UTP labelled riboprobes essentially as described (O. H. Sudin et al., Develop., 108:47; and B. Lutz et al., Develop., 120:25 [1994]). Briefly, pBluescript-Chk1 was linearized using either BstEI and sense and antisense transcripts were generated using either T7 or T3 polymerase, respectively. Specimens were photographed by double exposure using darkfield illumination with a red filter and Hoechst epifluorescence optics.

In addition to the in situ hybridization with murine tissues, FISH hybridization was used to map the genomic fragment containing hchk1. For this analysis, metaphase chromosomes prepared from human cells (peripheral blood lymphocytes) were tested with fluorescently-labelled human chk1 DNA, as known in the art (See e.g., J. W. Ijdo et al., Genomics 14:1019–1025 [1992]). Briefly, the longest cDNA obtained from the human B cell library (See, Example 1) was subcloned into pBlueScript (Stratagene), and used as a probe to screen a human genomic library in the BAC vector by hybridization as described by the manufacturer (Genome Systems). One clone designated "BACH-190 (C16)" (Genome Systems control number 12883) was analyzed by PCR. The PCR conditions were the same as those described in Example 1 above, with the exceptions being that a 42° C. annealing temperature was used, and two primer pairs (primers 186 and 484; and 415 and 177) were used. The sequences of the primers are shown below:

| | |
|---|---|
| Primer 177: | 5'-cta gag gag cag aat cg-3' (SEQ ID NO:12) |
| Primer 186: | 5'-gca gtt tgc agg aca gga taa tct tct cta gga ag-3' (SEQ ID NO:13) |

-continued

| | |
|---|---|
| Primer 415: | 5'-ttg ctc cag aac ttc tg-3' (SEQ ID NO:14) |
| Primer 484: | 5'-tat tgg ttg act tcc ggc-3' (SEQ ID NO:15) |

By automated sequence analysis, it was determined that this clone contained the chk1 sequence. This clone was then used in FISH analysis as known in the art, in order to determine the chromosomal location of the chk1 gene.

The results of this analysis placed the gene at a position that is adjacent to the gene encoding ATM on chromosome 11 (i.e., at 11q23). Loss of heterozygosity at this region has been associated with a number of cancers, including breast, lung, and ovarian cancers (I. Vorechovsky et al., Cancer Res., 56:2726 [1996]; and H. Gabra et al, Cancer Res., 56:950 [1996]).

In the Northern analyses, mRNAs from human and mouse tissues were hybridized with 25 ng of labeled human or mouse cDNAs, as appropriate, overnight in 50 mM PIPES, 100 mM NaCl, 50 mM $Na_2HPO_4$, 1 mM EDTA, and 5% SDS, at 65° C. The blots were washed in PIPES at room temperature, followed by a high stringency wash in 0.1×SSC with 0.5% SDS, at 65° C., for 40 minutes.

The results of the Northern blot analysis (as shown in FIGS. 5A and 5B), revealed the ubiquitous expression of hChk1, with large amounts present in human thymus, testis, small intestine, and colon. In adult mice, mChk1 was detected in all tissues examined, and large amounts were found in the testis, spleen and lung. In addition, mouse embryos from embryonic day 15.5 also revealed ubiquitous expression, with large amounts detected in the brain, liver, kidney, pancreas, intestines, thymus, and lung. These results were of particular interest, as testis, spleen, and thymus have also been found to express large amounts of ATM (G. Chen and E. Y. H. P. Lee, J. Biol. Chem., 271:33693 [1996]; and N. D. Lakin et al., Oncogene 13:2707 [1996]).

EXAMPLE 3

Antibodies Against Chk1

In this Example, affinity-purified antibodies to hChk1 protein ("anti-FL") and the 15 amino acids present on the carboxy terminus of the hChk1 protein ("anti-PEP") were produced. In these experiments, hChk1 protein was first produced in baculovirus as described below.

Recombinant baculovirus encoding glutathione S-transferase (GST) fusion proteins to hCHk1 (GST-hChk1) or a to a mutation of hChk1 in which Asp at position 130 was mutated to Ala (GST-hChk1 (D130A) were produced. Recombinant baculovirus encoding GST-hChk1 and GST-hChk1(D130A) (pYS71) were made by introducing an NdeI at the first ATG of the hChk1 open reading frame (ORF) using PCR, and subcloning the hChk1 cDNA as an Nde I-EcoRI fragment into pGEX2Tcs (Invitrogen) to generate pYS45. The XbaI-EcoRI fragment from pYS45 containing GST-hChk1 was then subcloned into pVL1393 (Invitrogen), which was cut with XbaI-EcoRI to generate pYS63.

The GST-hChk1(D130A) mutant was generated by the PCR and the XhoI-XmnI fragment containing the mutation was used to replace the wild-type fragment to generate pYS64. The hGST-Chk1(D130A) fragment from pYS64 was then subcloned into the baculovirus transfer vector using the Univector plasmid fusion strategy, as described in co-pending U.S. patent application Ser. No. 08/864,224, hereby incorporated by reference.

Viruses were generated by standard methods (e.g., Baculogold, Pharmingen). Recombinant GST-hChk1 protein was isolated from infected Hi5 insect cells (Invitrogen) on glutathione (GSH) agarose (Pharmacia).

The GST-hChk1 protein was then used to produce affinity-purified antibodies. In addition, antibodies directed against the carboxy-terminal 15 amino acids were produced using synthetically produced sequence. Recombinant GST-hChk1 was affinity purified from the cell lysate by chromatography on Glutathione Sepharose 4B (Pharmacia) according to the manufacturer's instructions.

Polyclonal antibodies against the purified GST-hChk1 or the carboxy terminal amino acids were generated in New Zealand white rabbits (Bethyl Laboratories), using standard techniques (See e.g., E. Harlow and D. Lane, *Antibodies: A Laboratory Manual,* Cold Spring Harbor Press, New York [1988]). Briefly, rabbits were given an initial immunization comprising 100 $\mu$g of affinity purified GST-hChk1 or the 15 amino acid sequence in complete Freund's adjuvant (CFA). The antigen was delivered by SC injection. The animals received boosts comprising 50 $\mu$g of affinity purified GST-hChk1 or 15 amino acid sequence, in incomplete Freund's adjuvant (IFA), as appropriate, at the following intervals day 14, day 28, day 42, day 56 and day 70. Sera were collected by bleeding the rabbits from the ear vein and the sera were prepared using standard techniques (E. Harlow and D. Lane, supra, at pp. 117 and 119). The anti-hCHk1 antibodies were referred to as "anti-FL," while the antibodies directed against the carboxy-terminal 15 amino acids were referred to as "anti-PEP."

Anti-PEP antibodies were purified using an affinity column that was prepared by coupling a peptide representing the carboxy-terminal 15 amino acids, at its N terminus to activated CH-Sepharose (Pharmacia) according to the manufacturer's instructions. The anti-FL antibodies were purified using an affinity column that was prepared by coupling the GST-Chk1 fusion protein from baculovirus to Affi-Gel 10 (Biorad) according to the manufacturer's directions. The antibody concentrations were roughly determined by Bradford analyses. The antibodies were subsequently tested in titration experiments and in Western blots, to determine their titer and specificity.

Affinity purified antibodies to these hChk1 protein made in baculovirus ("anti-FL") or to its COOH-terminal 15 amino acids ("anti-PEP"), recognized a 54-kD protein (FIG. 6) that comigrates with hChk1 expressed in baculovirus. The anti-PEP but not anti-FL signal is competed by addition of excess peptide indicating that the two sera are recognizing different hChk1 epitopes, further confirming identity of the 54-kD band as endogenous hChk1. A 70-kD protein was also specifically recognized by anti-PEP.

Antibodies directed against mChk1 were also produced and purified, using the same methods as described above for the anti-hChk1 antibodies.

mChk1 expressed from the cytomegalovirus promoter, CMV, in baby hamster kidney cells (BHK) resulted in detection of a 54-kD nuclear protein only in transfected cells using antibodies directed against the C-terminal peptide of mChk1. These (and all other transfections) were carried out as follows. Tissue culture flasks (T25) at 70–80% confluence were incubated with 3–9 $\mu$g DNA and 15–18 $\mu$l lipofectamine (Gibco BRL), in 3 ml of OptiMEMI (Gibco BRL), for 5–7 hours at 37° C. The cells were washed three times with Dulbecco's PBS without calcium or magnesium, and fed with DMEM with high glucose (Gibco BRL) and 10% FBS (Gibco BRL). The cells were harvested for Western blots or FACS analyses 48 hours post transfection. The results indicated exogenous mChk1 comigrates with endogenous mChk1 from mouse lung tissue.

EXAMPLE 4

Effect of DNA Damage

To determine whether hChk1 is modified in response to DNA damage like spChk1, hChk1 protein in extracts from cells treated with ionizing radiation was examined.

In the first set of experiments, HeLa cells were synchronized with 2 mM thymidine, and treated without (−) or with (+) 10 Gy of ionizing radiation one hour after release from the block. Cells were collected in G2-M, and extracts were fractionated by 10% SDS-PAGE, and immunoblotted with anti-PEP.

In addition to the HeLa cells, Jurkat cells were treated (+IR) or not treated (−IR) with 10 Gy of ionizing radiation and incubated for two hours. Extracts from these cells were resolved in the first dimension by using isoelectric focusing (IEF), with pH 3 to 10 ampholytes, and in the second dimension on a 10% SDS-PAGE, followed by immunoblotting with anti-PEP.

hChk1 from extracts from damaged cells showed a minor but reproducible reduction in mobility compared to $Chk1^{Hs}$ from untreated cells (FIG. 7). This modification was confirmed by 2-dimensional gel analysis which clearly demonstrated the generation of a more negatively charged Chk1 species 2 hours after γ-irradiation (FIG. 7). These results indicate that hChk1 may participate in transduction of the DNA damage signal like spChk1.

Indirect immunofluorescence was also conducted. In these experiments, human fibroblasts were fixed, stained with 4'6'-diamidino-2-phenylindole (DAP) to detect DNA, and were probed with affinity-purified anti-PEP, biotinylated antibody to rabbit IgG, and Texas Red streptavidin to reveal the subcellulai location of the hChk1 protein. This indirect immunofluorescence revealed that hChk1 is localized to the nucleus in a punctate staining pattern, similar to that observed for ATM.

mChk1 was also tested as described above for hChk1, with the exception that it was expressed in BHK cells. These results also confirmed the nuclear localization of mChk1.

Finally, in order to test for the ability of $Chk1^{Hs}$ to regulate the cell cycle, hChk1 or hChk1 (D130A) were transfected under the control of the cytomegalovirus (CMV) promoter, or the CMV vector alone into HeLa cells treated with and without 6 Gy of ionizing radiation. These transfections were accomplished as described in Example 3, above. No perturbation of the cell cycle by either kinase relative to vector alone was detected, suggesting that overproduction alone was insufficient to deregulate the system.

EXAMPLE 5

Phosphorylation of Cdk Tyrosine Phosphorylation Regulators

In this Example, the effects of phosphorylation of key regulators of Cdk tyrosine phosphorylation by chk1 was investigated.

Tyrosine phosphorylation of Cdc2 has been implicated in cell cycle arrest in response to DNA damage and replication blocks in both *S. pombe* (T. Enoch and P. Nurse, Cell 60:665 [1990]), and humans (P. Jin et al., J. Cell Biol., 134:963 [1996]). In *S. pombe,* Cdc2 mutants that cannot be phosphorylated on tyrosine display an inability to arrest the cell cycle in response to blockade of DNA replication. Although it was originally thought that the DNA damage checkpoint did not operate through tyrosine phosphorylation, tyrosine phosphorylation is apparently required for *S. pombe* cells to arrest in response to DNA damage. While it is now clear that tyrosine phosphorylation is required for proper checkpoint control, the experiments implicating tyrosine phosphorylation in this pathway do not distinguish between a regulatory role in which tyrosine phosphorylation rates are manipulated by the checkpoint pathways, or a passive role in which tyrosine phosphorylation is required to allow cell cycle arrest, but is not the actual target of the checkpoint pathway (S. J. Elledge, Science 274:1664 [1996]; and D. J. Lew and S. Kombluth, Curr. Opin. Cell. Biol., 8:795 [1996]).

Next, the ability of hChk1 to phosphorylate key regulators of Cdk tyrosine phosphorylation, the Cdc25 dual specificity phosphatases, hCdc25A, hCdc25B, and hCdc25C was analyzed. These regulators were chosen for several reasons. First, overproduction of hCdk4 mutants in which the inhibitory tyrosine is changed to phenylalanine abrogates G1 arrest in response to UV light (Y. Terada et al., Nature 376:358 [1995]). Secondly, the UV-sensitivity of $chk1^-$ mutants in *S. pombe* is suppressed by inactivating cdc25 with a Ts mutation (N. C. Walworth et al., Nature 363:368 [1993]). Finally, in *S. pombe* wee1mik1 mutants, DNA damage still causes a partial cell cycle delay that could be due to regulation of spCdc25 activity.

GST-hChk1 and GST-hChk1(D130A) were introduced into baculovirus, purified from baculovirus-infected insect cells as described in Example 3 above, and incubated with either GST, $His_6$-Cdc25C, GST-hCdc25A, hGST-Cdc25B, GST-hCdc25C, or GST-Cdc25C(200–256), and ($\gamma^{32}$P)ATP.

Figure 8B:
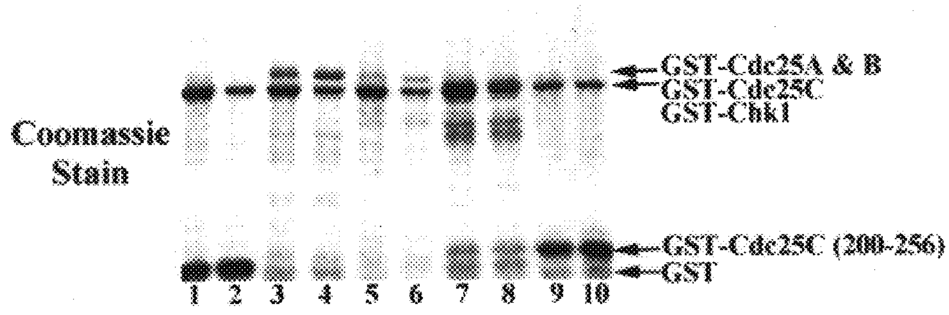
FIG. 8B is a Coomassie stained gel of FIG. 8A, showing the amount of each protein that is present in each lane.

The kinase reactions contained hGST-Chk1 bound to GSH agarose and either $His_6$-Cdc25C, GST-Cdc25A, GST-Cdc25B, GST-Cdc25C or GST-Cdc25C(200 to 256) (i.e., amino acids 200 to 256 of Cdc25). Kinase reactions contained 1 to 3 μg of GST-hChk1 or GST-hChk1(D130A) protein on beads and soluble substrate in 20 mM Hepes (pH 7.4), 10 mM $MgCl_2$, 10 mM $MnCl_2$, 2 μM ATP and 15 μCi ($\gamma$-$^{32}$P)ATP for 30 minutes at 30° C. The proteins were resolved by SDS-PAGE (10%), and visualized by autoradiography for kinase assays (FIG. 8A), or by Coomassie staining (FIG. 8B). Less GST-Cdc25B was loaded than the other substrates (approximately ⅕ of the other substrates was loaded).

GST-Chk1 phosphorylated all three Cdc25 proteins but not GST alone (FIG. 8). Although Gst-$Cdc25C^{Hs}$ co-migrated with Gst-$Chk1^{Hs}$ which autophosphorylates, increased phosphorylation was observed at that position relative to that in the presence of kinase alone and phosphorylation of a Gst-$Cdc25C^{Hs}$ breakdown product was visible.

Figure 10:
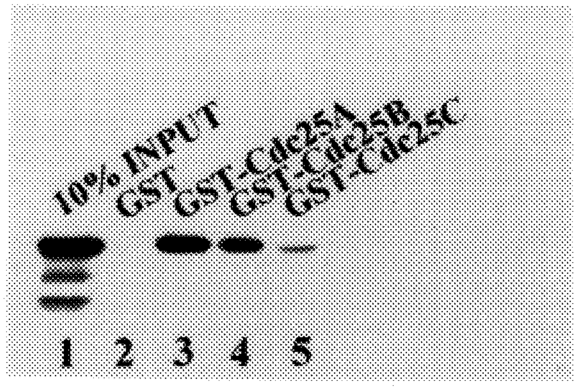
FIG. 10 shows Chk1 binding to GST-Cdc25A, GST-Cdc25B and GST-Cdc25C by immunoblotting with anti Chk1 antibodies.

Protein kinases often form complexes with their substrates. To examine this for hChk1, and the Cdc25 proteins, GST-Cdc25 proteins present on glutathione beads were incubated together with baculovirus extracts expressing $His_6$-tagged hChk1, and precipitated. GST-hCdc25A, GST-hCdc25B, and GST-hCdc25C each specifically bound hChk1, while GST alone did not (FIG. 10). Furthermore, two other GST fusion proteins, GST-Dun1 and GST-Skp1, all failed to bind hChk1. These results indicate that Cdc25 can form complexes with hChk1.

To determine the site on Cdc25C that is phosphorylated by hChk1, the kinase reactions were carried out in a buffer consisting of 50 mM Tris (pH 7.4), 10 mM $MgCl_2$, 10 μM ATP, 1 mM DTT and 10 $\mu$Ci ($\gamma$-$^{32}$P)ATP. The proteins were separated by SDS-PAGE, transferred to nitrocellulose membranes, and visualized by autoradiography. The nitrocellulose membrane containing His-Cdc25C was excised, blocked with 0.5% polyvinylpyrrolidone (PVP-40) in 100 mM acetic acid for 30 minutes at 37° C., washed six times with water, and digested with TPCK trypsin (Worthington) at a final concentration of 30 mg/ml, in 0.1 M $NH_4CO_3$ (pH 8.0). Further digestion on selected HPLC fractions was performed with 2 units of proline specific endopeptidase (ICN) in 0.1M sodium phosphate, 5 mM EDTA (pH 7.4), at 37° C. for 16 hours. Samples were acidified in 1% trifluoroacetic acid (TFA) and loaded onto a Vydac C18 column (25 cm×0.46 cm inner diameter). Reverse phase HPLC was performed at 37° C. Reactions were loaded in 0.1% TFA (Buffer A) and eluted with a gradient from 0 to 60% Buffer B (90% acetonitrile, 0.095% TFA). Fractions were collected at 0.5 minutes intervals up to 90 minutes, and counted for radioactivity. Selected fractions were immobilized on Sequenlon-AA membrane discs (Millipore) for $NH_2$-terminal sequencing. Manual Edman degradation was done as known in the art (See, J. E. Bodwell et a., J. Biol. Chem., 266:7549 [1991]; and S. Sullivan, and T. W. Wong, Anal. Biochem., 197:65 [1991]) with a coupling and cleavage temperature of 55° C.

To establish the significance of the Cdc25 phosphorylation, the site of Chk1$^{Hs}$ phosphorylation on Cdc25C was mapped. Ser 216 is the main site of phosphorylation of Cdc25C$^{Hs}$ in vivo. hChk1 phosphorylated a 56 amino acid region of the hCdc25C protein fused to GST, but not GST alone (FIG. 8). This 56 amino acid motif contains 4 possible sites of phosphorylation. Peptide analysis of proteolytic fragments of full length His$_6$-hCdc25C phosphorylated with GST-hChk1 revealed a single phosphorylated tryptic peptide by high pressure liquid chromatography. Edman degradation of this peptide indicated release of radioactivity in the third cycle (FIG. 12B). FIG. 12A shows the radioactivity measured from column fractions obtained during reverse phase HPLC. Further degradation of this tryptic fragment with proline endopeptidase resulted in a peptide that released radioactivity in the first cycle. Serine 216 is the only site on Cdc25C$^{Hs}$ consistent with this phosphorylation pattern (FIG. 11), as amino acids inclusive of and surrounding Serine$^{216}$ contain amino-terminal trypsin and proline endopeptidase cleavage sites.

Figure 9A:
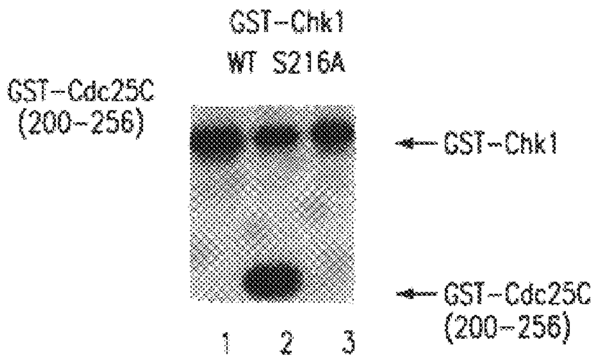
FIG. 9A is an autoradiograph showing radiolabeled phosphate incorporation due to phosphorylation of Chk1 and wild-type Cdc25C(200–256).
Figure 9B:
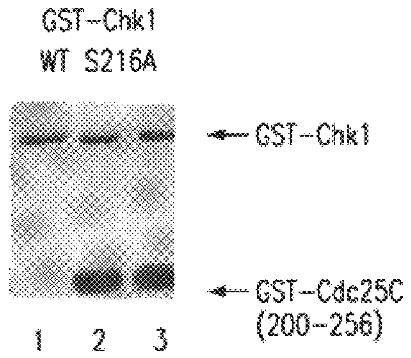
FIG. 9B is a Coommassie-stained gel of FIG. 9A, showing the amount of each protein present in each lane.
Figure 9C:
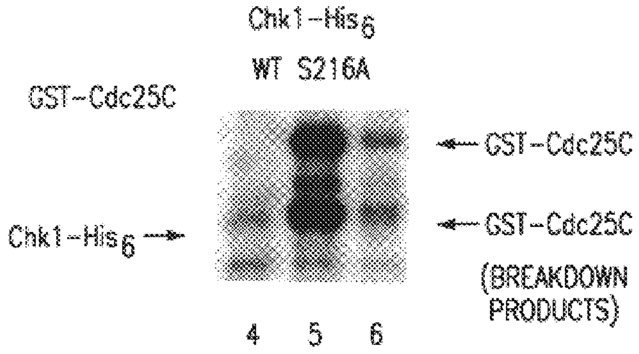
FIG. 9C is an autoradiograph showing radiolabeled phosphate incorporation due to phosphorylation of Chk1 and wild-type Cdc25C.
Figure 9D:
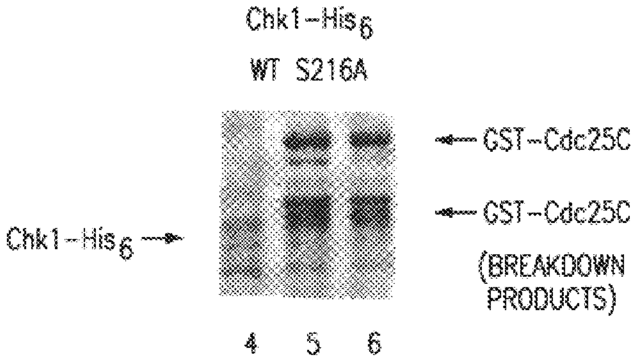
FIG. 9D is a Coomassie-stained gel of FIG. 9C, showing he amount of each protein present in each lane.

In addition, GST-hChk1 purified from baculovirus was incubated with either GST-hCdc25C(200–256) or GST-hCdc25C(200–256)(S216A), and ($\gamma$-$^{32}$P)ATP, using the same methods as described above. The results are shown in FIG. 9A). In addition, hChk 1-His$_6$ purified from baculovirus was incubated with either GST-hCdc25C (lane 5, FIG. 9B), or GST-hCdc25C(S216A) and ($\gamma$-$^{32}$P)ATP. Proteins were resolved and visualized as described above. As shown in FIG. 9, there was clear phosphorylation of GST-hCdc25C. A catalytically inactive mutant (GST-hChk1(D130A)(k-) failed to phosphorylate itself or any of the Cdc25 proteins (See, FIG. 9).

To confirm this, the Cdc25C S216A mutation in Gst-Cdc25C and Cdc25C(200–256) were constructed. Both were found to be poor substrates for hChk1 confirming S216 as the site phosphorylation (FIG. 11). S216 has also been reported to be phosphorylated by spChk1, demonstrating phylogenetic conservation of this regulatory relationship.

EXAMPLE 6

Production of Monoclonal Antibodies

The antibodies of the present invention may be monoclonal or polyclonal. Thus, it is within the scope of this invention to include other (e.g., second antibodies) (monoclonal or polyclonal) directed against or similar to the first antibodies discussed above. It is contemplated that these antibodies will find use in detection assays. Both the first and second antibodies may be used in the detection assays or a first antibody may be used with a commercially available anti-immunoglobulin antibody. An antibody as contemplated herein includes any antibody specific to any region of human or murine Chk1.

The production and use of monoclonal antibodies in an immunoassay is an alternative method to that described in Example 3. Monoclonals provide some advantages because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See e.g., Douillard and Hoffman, Basic Facts about Hybridomas, in *Compendium of Immunology* Vol II, ed. by Schwartz [1981]; Kohler and Milstein, Nature 256:495–499 [1975]; Eur. J. Immunol., 6:511–519, [1976]).

Unlike preparation of polyclonal sera, the choice of animal is dependent on the availability of appropriate immortal lines capable of fusing with lymphocytes. Mouse and rat have been the animals of choice in hybridoma technology and are preferably used. Humans can also be utilized as sources for sensitized lymphocytes if appropriate immortalized human (or nonhuman) cell lines are available. For the purpose of the present invention, the animal of choice may be injected with an antigenic amount, for example, from about 0.1 mg to about 20 mg of the enzyme or protein or antigenic parts thereof. Usually the injecting material is emulsified in Freund's complete adjuvant. Boosting injections may also be required. The detection of antibody production can be carried out by testing the antisera with appropriately labelled antigen. Lymphocytes can be obtained by removing the spleen of lymph nodes of sensitized animals in a sterile fashion and carrying out fusion. Alternatively, lymphocytes can be stimulated or immunized in vitro, as described, for example, in Reading, J. Immunol. Meth., 53:261–291 [1982]).

A number of cell lines suitable for fusion have been developed and the choice of any particular line for hybridization protocols is directed by any one of a number of criteria such as speed, uniformity of growth characteristics, deficiency of its metabolism for a component of the growth medium, and potential for good fusion frequency.

Intraspecies hybrids, particularly between like strains, work better than interspecies fusions. Several cell lines are available, including mutants selected for the loss of ability to secrete myeloma immunoglobulin.

Cell fusion can be induced either by virus, such as Epstein-Barr or Sendai virus, or polyethylene glycol. Polyethylene glycol (PEG) is the most efficacious agent for the fusion of mammalian somatic cells. PEG itself may be toxic for cells and various concentrations should be tested for effects on viability before attempting fusion. The molecular weight range of PEG may be varied from 1000 to 6000. It gives best results when diluted to from about 20% to about 70% (w/w) in saline or serum-free medium. Exposure to PEG at 37° C. for about 30 seconds is preferred in the present case, utilizing murine cells. Extremes of temperature (i.e., about 45° C.) are avoided, and preincubation of each component of the fusion system at 37° C. prior to fusion can be useful. The ratio between lymphocytes and malignant cells is optimized to avoid cell fusion among spleen cells and a range of from about 1:1 to about 1:10 is commonly used.

The successfully fused cells can be separated from the myeloma line by any technique known by the art. The most common and preferred method is to choose a malignant line which is Hypoxthanine Guanine Phosphoribosyl Transferase (HGPRT) deficient, which will not grow in an aminopterin-containing medium used to allow only growth of hybrids and which is generally composed of hypoxthanine $1\times10^{-4}$ M, aminopterin $1\times10^{-5}$M, and thymidine $3\times10^{-5}$M, commonly known as the HAT medium. The fusion mixture can be grown in the HAT-containing culture medium immediately after the fusion 24 hours later. The feeding schedules usually entail maintenance in HAT medium for two weeks and then feeding with either regular culture medium or hypoxthanine, thymidine-containing medium.

The growing colonies are then tested for the presence of antibodies that recognize the antigenic preparation. Detection of hybridoma antibodies can be performed using an assay where the antigen is bound to a solid support and allowed to react to hybridoma supernatants containing putative antibodies. The presence of antibodies may be detected by "sandwich" techniques using a variety of indicators. Most of the common methods are sufficiently sensitive for use in the range of antibody concentrations secreted during hybrid growth.

Cloning of hybrids can be carried out after 21–23 days of cell growth in selected medium. Cloning can be preformed by cell limiting dilution in fluid phase or by directly selecting single cells growing in semi-solid agarose. For limiting dilution, cell suspensions are diluted serially to yield a statistical probability of having only one cell per well. For the agarose technique, hybrids are seeded in a semi-solid upper layer, over a lower layer containing feeder cells. The colonies from the upper layer may be picked up and eventually transferred to wells.

Antibody-secreting hybrids can be grown in various tissue culture flasks, yielding supernatants with variable concentrations of antibodies. In order to obtain higher concentrations, hybrids may be transferred into animals to obtain inflammatory ascites. Antibody-containing ascites can be harvested 8–12 days after intraperitoneal injection. The ascites contain a higher concentration of antibodies but include both monoclonals and immunoglobulins from the inflammatory ascites. Antibody purification may then be achieved by, for example, affinity chromatography.

Antibodies produced by these methods can then be used in immunoassay methods to detect human or murine Chk1. Such methods include, but are not limited to ELISA (enzyme-linked immunosorbent assay), IFA (immunofluorescence assay), or RIA (radioimmunoassay).

From the above it should be clear that the present invention provides gene sequences encoding mammalian checkpoint genes and proteins useful as probes for a tumors and other malignancies, as well as growth and/or development deficiencies.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated nucleotide sequence set forth in SEQ ID NO:3.

2. The isolated nucleotide sequence of claim 1, wherein said isolated nucleotide sequence further comprises operative 5' and 3' flanking regions.

3. An isolated genomic DNA sequence encoding the polypeptide of SEQ ID NO:1.

4. An isolated nucleotide sequence which encodes the polypeptide of SEQ ID NO:1.

5. An isolated polynucleotide sequence which is the complement of SEQ ID NO:3 and which specifically hybridizes to the sequence of SEQ ID NO:3.

6. An isolated recombinogenic vector comprising the nucleotide sequence of claim 1.

7. An isolated recombinogenic host cell containing the vector of claim 6.

8. An isolated nucleotide sequence set forth in SEQ ID NO:4.

9. The isolated nucleotide sequence of claim 8, wherein said isolated nucleotide sequence further comprises operative 5' and 3' flanking regions.

10. An isolated genomic DNA sequence encoding the polypeptide of SEQ ID NO:2.

11. An isolated nucleotide sequence which encodes the polypeptide of SEQ ID NO:2.

12. An isolated polynucleotide sequence which is the complement of SEQ ID NO:4 and which specifically hybridizes to the sequence of SEQ ID NO:4.

13. An isolated recombinogenic vector comprising the nucleotide sequence of claim 8.

14. An isolated recombinogenic host cell containing the vector of claim 13.

15. A method for the detection of polynucleotides encoding human Chk1 in a biological sample comprising the steps of:

a) hybridizing a polynucleotide sequence which comprises at least a portion of a nucleotide sequence of SEQ ID NO:3 and which specifically hybridizes to the complement of SEQ ID NO:3 to nucleic acid material of a biological sample, thereby forming a hybridization complex; and b) detecting said hybridization complex, wherein the presence of said complex correlates with the presence of a polynucleotide encoding human Chk1 in said biological sample.

16. The method of claim 15, wherein before hybridization, the nucleic acid material of the biological sample is amplified by the polymerase chain reaction.

17. The method of claim 16, wherein said polymerase chain reaction is conducted using primers selected from the group consisting of SEQ ID NOS:5, 6, 12, 13, 14, and 15.

* * * * *